United States Patent
Tovey et al.

(10) Patent No.: US 12,025,620 B2
(45) Date of Patent: *Jul. 2, 2024

(54) SYSTEM AND PRODUCTS FOR IMPROVED QUANTIFICATION OF ADCC AND ADCP ACTIVITY

(71) Applicant: SVAR LIFE SCIENCE AB, Malmö (SE)

(72) Inventors: Michael Tovey, Paris (FR); Christophe Lallemand, Paris (FR)

(73) Assignee: SVAR LIFE SCIENCE AB, Malmö (SE)

( * ) Notice: Subject to any disclaimer, the term of this patent is extended or adjusted under 35 U.S.C. 154(b) by 804 days.

This patent is subject to a terminal disclaimer.

(21) Appl. No.: 16/981,947

(22) PCT Filed: Mar. 14, 2019

(86) PCT No.: PCT/EP2019/056403
§ 371 (c)(1),
(2) Date: Sep. 17, 2020

(87) PCT Pub. No.: WO2019/179871
PCT Pub. Date: Sep. 26, 2019

(65) Prior Publication Data
US 2021/0072256 A1  Mar. 11, 2021

(30) Foreign Application Priority Data

Mar. 19, 2018 (EP) .................................... 18162485

(51) Int. Cl.
*G01N 33/68* (2006.01)
*C07K 14/705* (2006.01)
*C07K 14/735* (2006.01)
*C07K 16/24* (2006.01)
*C07K 16/28* (2006.01)

(52) U.S. Cl.
CPC ... *G01N 33/6854* (2013.01); *C07K 14/70532* (2013.01); *C07K 14/70535* (2013.01); *C07K 16/241* (2013.01); *C07K 16/2863* (2013.01); *C07K 2317/732* (2013.01)

(58) Field of Classification Search
None
See application file for complete search history.

(56) References Cited

FOREIGN PATENT DOCUMENTS

| WO | WO 2015/179833 A1 | 11/2015 |
| WO | WO 2016/040441 A1 | 3/2016 |
| WO | WO 2017/186121 A1 | 11/2017 |
| WO | WO 2018/065401 A1 | 4/2018 |
| WO | WO 2018/140960 A1 | 8/2018 |
| WO | WO 2018/151817 A2 | 8/2018 |
| WO | WO 2018/185301 A1 | 10/2018 |

OTHER PUBLICATIONS

Machine English Translation WO 2017186121 (Year: 2017).*
Cheng et al., "Development of a robust reporter-based ADCC assay with frozen, thaw-and-use cells to measure Fc effector function of therapeutic antibodies" Journal of Immunological Methods 2014, 414: 69-81.
Lallemand et al., "Reporter gene assay for the quantification of the activity and neutralizing antibody response to TNFα antagonists" Journal of Immunological Methods 2011, 373:229-239.
Lallemand et al., "A Novel System for the Quantification of the ADCC Activity of Therapeutic Antibodies" Journal of Immunology Research 2017, vol. 2017, 19 pages.
Parekh et al., "Development and validation of an antibodydependent cell-mediated cytotoxicity-reporter gene assay" mAbs May/Jun. 2012; 4(3):310-318.
Sallin et al., "The anti-lymphoma activities of anti-CD137 monoclonal antibodies are enhanced in FcγRIII(−/−) mice" Cancer Immunol Immunother. Sep. 2014; 63(9):947-58.
Tatsumi et al., "Expression of Costimulatory Molecules B7-1 (CD80) and B7-2 (CD86) on Human Hepatocellular Carcinoma." Hepatology 1997, 25(5):1108-1114.

* cited by examiner

*Primary Examiner* — Changhwa J Cheu
(74) *Attorney, Agent, or Firm* — Casimir Jones SC; Lisa Mueller

(57) ABSTRACT

The present invention relates novel cells and their use in methods for determining the antibody-dependent cell-mediated cytotoxicity (ADCC) or antibody-dependent cell-mediated phagocytosis (ADCP) in a sample.

17 Claims, 34 Drawing Sheets
Specification includes a Sequence Listing.

|  | Eff V / CD20 | Eff V / CD80 | Eff V / CD86 |
|---|---|---|---|
| Upper asymptote | 347363 | 347263 | 210818 |
| Lower asymptote | 4428 | 4272 | 3124 |
| HillSlope | 1,297 | 1,475 | 1,127 |
| EC50 (ng / ml) | 48,13 | 119,5 | 51,18 |
| Fold induction | 128,2 | 99,45 | 65,4 |

| | Eff V CD28 / ErbB2 | Eff V CD28 / ErbB2 CD80 | Eff V CD28 / ErbB2 CD86 | Eff V CD28 / ErbB2 CD80 / CD86 | Eff V NFAT / SKBr3 |
|---|---|---|---|---|---|
| Upper Asymptote | 435,831 | 1,927,158 | 4,137,595 | 4,381,741 | 1,542,574 |
| Lower Asymptote | 2,259 | 12,938 | 8,444 | 18,012 | 35,614 |
| HillSlope | 1.009 | 1.048 | 1.027 | 1.271 | 1.426 |
| EC50 | 16.45 | 4.74 | 2.191 | 9.578 | 56.09 |
| Fold Induction | 166 | 168 | 476 | 228 | 46 |

|  | Eff F CD28 / ErbB2 | Eff F CD28 / ErbB2 CD86 | Eff F NFAT / SKBr3 |
|---|---|---|---|
| Upper Asymptote | 108,290 | 1,405,665 | 333,935 |
| Lower Asymptote | 10,550 | 7,563 | 29,306 |
| HillSlope | 2.462 | 1.922 | 1.951 |
| EC50 | 117.9 | 160.3 | 72.9 |
| Fold Induction | 10 | 193 | 11 |

|  | Eff V/ EGFR | Eff V/ EGFR CD80 | Eff V/ EGFR CD86 | Eff V/ EGFR CD80/CD86 | Eff V NFAT/ A431 |
|---|---|---|---|---|---|
| Upper Asymptote | 26,648 | 250,063 | 514,312 | 847,023 | 2,139,934 |
| Lower Asymptote | 1,007 | 2,238 | 2,154 | 1,982 | 30,242 |
| HillSlope | 1.547 | 1.34 | 1.258 | 1.68 | 1.46 |
| EC50 | 21.6 | 9.914 | 18.26 | 26.74 | 37.09 |
| Fold Induction | 27 | 109 | 256 | 485 | 63 |

| | Eff F CD28 / EGFR | Eff F CD28 / EGFR CD86 | Eff F NFAT / A431 |
|---|---|---|---|
| Upper Asymptote | 7,644 | 46,294 | 186,111 |
| Lower Asymptote | 5,550 | 5,563 | 22,934 |
| HillSlope | 0.2109 | 3.085 | 2.522 |
| EC50 | | 56 | 63.89 |
| Fold Induction | 1 | 8 | 8 |

| | Eff F CD28 / EGFR | Eff F CD28 / EGFR CD86 | Eff F NFAT / A431 |
|---|---|---|---|
| Upper Asymptote | 7,644 | 46,294 | 186,111 |
| Lower Asymptote | 5,550 | 5,563 | 22,934 |
| HillSlope | | 3.085 | 2.522 |
| EC50 | | 56 | 63.89 |
| Fold Induction | | 8 | 8 |

| | Eff F CD28 / mTNF | Eff F CD28 / mTNF CD80 | Eff F CD28 / mTNF CD86 |
|---|---|---|---|
| Upper Asymptote | 64,400 | 152,500 | 143,841 |
| Lower Asymptote | 33,763 | 44,875 | 54,553 |
| HillSlope | 27.78 | 16.2 | 3.908 |
| EC50 | 34.31 | 34.29 | 44.53 |
| Fold Induction | 2.018 | 3.348 | 2.707 |

Table 1

| Target Cell | CD20++ | CD80 | CD86 | CD80/86 | CD20++ | CD80 | CD86 | CD80/86 |
|---|---|---|---|---|---|---|---|---|
| Best Fit Values | | | | | | | | |
| Upper Asymptote | 519,549 | 713,632 | 524,127 | 638,074 | 1,098,073 | 1,492,550 | 1,082,758 | 987,610 |
| Lower Asymptote | 2235 | 2290 | 2065 | 2670 | 12,250 | 17,950 | 12,750 | 24,450 |
| Hill Slope | 0,933 | 0,864 | 0,8285 | 0,887 | 0,9121 | 0,8319 | 0,8783 | 0,8462 |
| $EC_{50}$ | 2,143 | 4,326 | 3,502 | 2,815 | 2,034 | 4,518 | 2,771 | 2,951 |
| Fold Induction | 232,9 | 312,2 | 253,9 | 239,7 | 83,15 | 83,45 | 85,38 | 40,34 |

FIG. 16

Table 2

| Target Cell | erbB2++ | CD80 | CD86 | CD80/86 | erbB2++ | CD80 | CD86 | CD80/86 |
|---|---|---|---|---|---|---|---|---|
| Best Fit Values | | | | | | | | |
| Upper Asymptote | 324,042 | 1,123,325 | 2,313,547 | 2,374,164 | 435,831 | 1,927,158 | 4,137,595 | 4,361,741 |
| Lower Asymptote | 1,418 | 1,739 | 1,741 | 2,064 | 2,259 | 12,938 | 8,444 | 18,012 |
| Hill Slope | 1.219 | 1.1 | 1.131 | 1.841 | 1.009 | 1.048 | 1.027 | 1.271 |
| $EC_{50}$ | 12.97 | 7.667 | 4.151 | 10.21 | 16.45 | 4.74 | 2.191 | 9.578 |
| Fold Induction | 297 | 658 | 1,314 | 1,142 | 166 | 168 | 476 | 228 |

FIG. 17

Table 3

| Effector Cell | EGFR++ | CD80 | CD86 | CD80/86 | EGFR++ | CD80 | CD86 | CD80/86 |
|---|---|---|---|---|---|---|---|---|
| Best Fit Values | | | | | | | | |
| Upper Asymptote | 26,648 | 250,063 | 514,312 | 847,023 | 46,735 | 555,768 | 1,020,128 | 1,373,801 |
| Lower Asymptote | 1,007 | 2,238 | 2,154 | 1,982 | 2523 | 11,696 | 10,112 | 16,454 |
| Hill Slope | 1.547 | 1.34 | 1.258 | 1.68 | 1.598 | 1.561 | 1.036 | 1.179 |
| $EC_{50}$ | 21.6 | 9.914 | 18.26 | 26.74 | 24.15 | 8.249 | 16.58 | 21.57 |
| Fold Induction | 27 | 109 | 256 | 485 | 17 | 50 | 86 | 86 |

FIG. 18

Table 4

| Target Cell | mTNFα++ | CD80 | CD86 | CD80/86 | mTNFα++ | CD80 | CD86 | CD80/86 |
|---|---|---|---|---|---|---|---|---|
| Best Fit Values | | | | | | | | |
| Upper Asymptote | 263,535 | 536,855 | 726,766 | 737,141 | 463,132 | 1,273,855 | 1,276,808 | 1,361,550 |
| Lower Asymptote | 7,272 | 8,224 | 10,319 | 12,532 | 18,931 | 50,855 | 65,344 | 75,734 |
| Hill Slope | 1.987 | 1.461 | 1.57 | 1.552 | 2.23 | 1.216 | 1.696 | 1.287 |
| $EC_{50}$ | 16.28 | 10.67 | 28.49 | 23.14 | 15.03 | 11.36 | 27.09 | 25.29 |
| Fold Induction | 33 | 61 | 69 | 57 | 27 | 26 | 19 | 18 |

FIG. 19

SYSTEM AND PRODUCTS FOR IMPROVED QUANTIFICATION OF ADCC AND ADCP ACTIVITY

CROSS REFERENCE TO RELATED APPLICATIONS

This application is a national phase application under 35 U.S.C. § 371 of PCT International Application No. PCT/EP2019/056403, filed Mar. 14, 2019, which claims priority to European Application No. 18162485.9, filed Mar. 19, 2018, which are hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 668 Byte ASCII (Text) file named "38757-251_ST25.TXT," created on Aug. 23, 2021.

FIELD OF THE INVENTION

The present invention relates novel cells and their use in methods for determining the antibody-dependent cell-mediated cytotoxicity (ADCC) or antibody-dependent cell-mediated phagocytosis (ADCP) in a sample. The cells according to the invention may be used in a kit or a kit of parts that may be used in a diagnostic context. Importantly, the cells according to the invention may be used to determine the effectiveness of a treatment based on e.g. antibodies or Fc fusion proteins.

BACKGROUND OF THE INVENTION

It is well known that the activity of a number of monoclonal antibodies is mediated in part by host-mediated effector cell function including ADCC and/or ADCP. The antibodies are directed to a specific antigen on a target cell, such as a tumor cell or an inflammation causing lymphocyte. Once bound to the target cell, the Fc receptor moiety of an effector cell will bind to the Fc portion of the monoclonal antibody and thereby effect killing of the target cell by the effector cell.

In order to quantitate the effectiveness of an antibody in such an ADCC or ADCP process, it is necessary to have effector cells, target cells, and control target cells that are used to determine the effectiveness of the antibody. In the prior art, one harvests endogenous effector cells, natural killer (NK), cells from human subjects and target cells from human subjects or established tumor cell lines and use those target cells in such testing. In the classic assay, the target cells are chromium loaded so that cell killing can be determined by release of the chromium. This method suffers many disadvantages, such as, one must harvest the effector cells used from human subjects and thus there is great variability in the cells being used for the quantification. Furthermore, it is difficult and expensive to obtain the cells in this manner. For example, there is substantial variation from donor to donor. Furthermore, for a negative control in this classical assay, one would use a cell line that does not express the target receptor, such as CD20 for rituximab and erbB2 for trastuzumab. Thus, for example, one would use a T cell line which does not express CD20. The disadvantage of the use of such a negative control target cell is, of course, that the cell differs in many respects in addition to the absence of CD20 expression to the target cell and does not constitute a good control.

Another disadvantage is that they are long and protracted assays and often have to be incubated overnight. The dynamic range is restricted and the sensitivity is poor. The dynamic range is the difference between the maximum achievable signal at the highest concentration of the drug and by the control and zero (no drug sample). Sensitivity is the activity generated by small quantities of antibody, i.e., the smaller the quantity of antibody necessary to generate detectable activity, the greater the sensitivity of the assay. Another disadvantage is that the assays are often imprecise rendering the detection of small differences between different variants of a monoclonal antibody difficult.

One improvement on this standard quantification assay has been described by Parekh at al (1) and modified and commercialized (2). In the assay, it is developed a recombinant effector cell line containing a NFAT responsive reporter gene construct that responds to binding of the Fc moiety of immunoglobunins to the FcγIIIa receptor (CD16) by activation of the firefly luciferase (FL) reporter gene and the emission of light that can be quantified in a luminomter. These effector cells are sold in a freeze, thaw and use format (3). It is an improvement over the standard lytic assay as it uses a surrogate marker of the ADCC mechanism that can be quantified in a much more sensitive manner with somewhat greater dynamic range in a much more convenient format, as one does not have to harvest the effector cells but one uses the freeze and thaw cells. Similarly, ADCP activity can also be quantified in a similar manner using effector cells that express FcγIIa (CD32) functionally linked to NFAT responsive firefly luciferase reporter-gene and wild type (WT) target cells. Such an ADCP effector cell line is available commercially (Promega Corporation Madison WI). The use of these cells together with WT target cells to assess the ADCP activity of an antibody results in an assay with a restricted dynamic range and limited sensitivity.

In addition, a novel recombinant effector cell line has been described recently (3) and disclosed in WO 2018/065401 in which the firefly luciferase (FL) reporter gene is regulated by a novel synthetic chimeric promoter containing binding sites for the principal transcription factors (NF-AT, AP1, NFkB, and STAT5) activated following the interaction of the Fc moiety of an antibody with the FcγRIIIA receptor on effector cells. Furthermore, a novel recombinant effector cell line is disclosed herein that expresses CD32 functionally linked to the firefly luciferase reporter-gene regulated by the same synthetic chimeric promoter as disclosed in WO 2018/065401. The recombinant effector cells expressing CD16 or CD32 functionally linked to the FL reporter-gene regulated by the chimeric promoter disclosed in WO 2018/065401 confer improved sensitivity and an improved dynamic range, relative to engineered effector cell lines that express a NFAT regulated reporter-gene, when used in an ADCC or ADCP assay respectively together with engineered target cells that over-express a constant high level of the specific antigen recognized by the antibody.

WO 2017/186121 relates to a method for improving the function of an immune response cell and an immune response cell which expresses at least one receptor capable of binding to an antigen and type I interferon. The cell has a significant ability to kill tumours or pathogens and can be used for treating tumours and infectious diseases.

Lallemand, C., et al., J. Immunol. Res., vol 2017, pp. 1-19, relates to novel ADCC effector cells expressing the V-variant or F-variant of FcγRIIIa (CD16a) and firefly luciferase under the control of a chimeric promoter incorporating recognition sequences for the principal transcription factors involved in FcγRIIIa signal transduction, together with novel target cells overexpressing a constant high level of the specific antigen recognized by rituximab, trastuzumab, cetuximab, infliximab, adalimumab, or etanercept, conferring improved sensitivity, specificity, and dynamic range in an ADCC assay relative to effector cells expressing a NFAT-regulated reporter gene and wild-type target cells.

Nevertheless, there is always a desire to further improve the quantitative ADCC and ADCP assays. It would be desirable to have an assay which has a much improved dynamic range, and improved sensitivity particularly for the quantification of ADCP activity.

The present invention relates to over-expression in an effector and/or target cell of one or more co-stimulatory molecules that results in a markedly enhanced dynamic range and increased sensitivity when said cells are used to assess the ADCC or ADCP activity of an antibody.

FIGURES

FIG. 16 illustrates Table 1, which illustrates the effect on an ADCC assay, expressed as the principal parameters of a 4PL plot, of overexpression of the co-stimulatory molecules CD80, CD86, and CD80 together with CD86 in $CD20^{++}$ target cells used in conjunction with iLite® effector cells expressing the V-variant of CD16A.

FIG. 17 illustrates Table 2, which illustrates the effect on an ADCC assay, expressed as the principal parameters of a 4PL plot, of overexpression of the co-stimulatory molecules CD80, CD86, and CD80 together with CD86 in $ERBB2^{++}$ target cells used in conjunction with iLite® effector cells expressing the V-variant of CD16A.

FIG. 18 illustrates Table 3, which illustrates the effect on an ADCC assay, expressed as the principal parameters of a 4PL plot, of overexpression of the co-stimulatory molecules CD80, CD86, and CD80 together with CD86 in $EGFR^{++}$ target cells used in conjunction with iLite® effector cells expressing the V-variant of CD16A.

FIG. 19 illustrates Table 4, which illustrates the effect on an ADCC assay, expressed as the principal parameters of a 4PL plot, of overexpression of the co-stimulatory molecules CD80, CD86, and CD80 together with CD86 in $mTNF\alpha^{++}$ target cells used in conjunction with iLite® effector cells expressing the V-variant of CD16A.

SUMMARY OF THE INVENTION

Figure 1A:
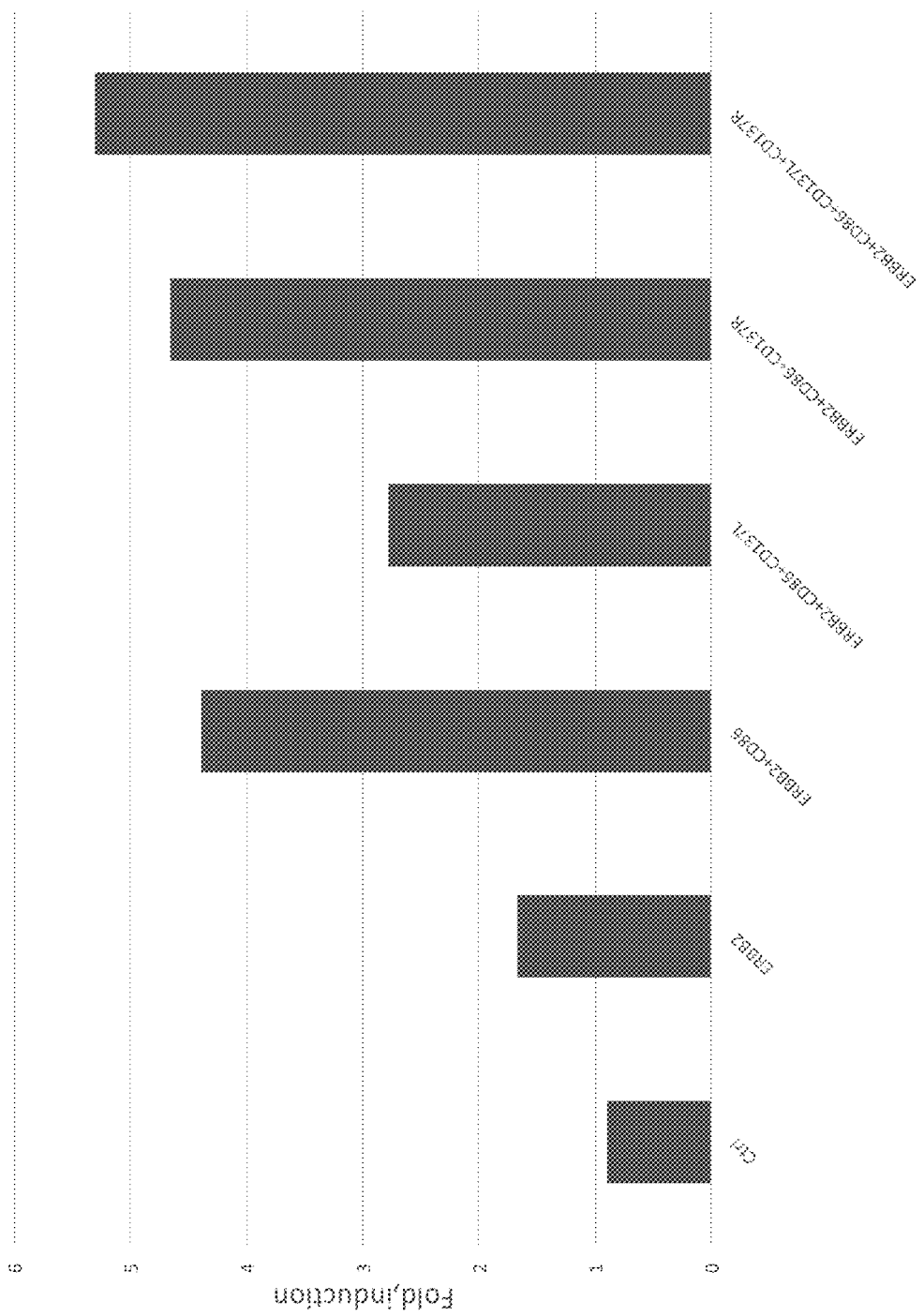
FIG. 1A illustrates a comparison of the ADCC activity of trastuzumab determined using the iLite® effector cells (V-variant) co-transfected or not with CD137 and HEK293 target cells over-expressing ERBB2 alone or overexpressing ERBB2 and CD86, or overexpressing ERBB2, CD86 and CD137L.

The present invention solves the above mentioned problems and provides i.a. a substantial improvement in the freeze, thaw and use effector cells and target cells of prior art assays so as to provide an improved sensitivity, and/or an improved dynamic range. In one aspect, the problem is solved by i.a. the aid of an engineered polynucleotide sequence comprised in a vector and ultimately a cell according to present invention.

In one aspect, the invention provides for a polynucleotide sequence, vector and ultimately engineered cells that provides for an improved sensitivity in an assay.

In another aspect, the invention provides for a polynucleotide sequence, vector and ultimately engineered cells that provides for an improved dynamic range in an assay.

In yet a further aspect, the invention provides for a polynucleotide sequence, vector and ultimately engineered cells that provides for an improved sensitivity in an assay and simultaneously an improved dynamic range in an assay.

The improved sensitivity manifests itself in a substantially improved $EC_{50}$ and LLOQ (Lower Limit of Quantification). Specifically, the present invention provides for a cell line and ultimately the use thereof in a kit for an increased sensitivity (measured as the EC50) or LLOQ which is at least about 10-fold in comparison with techniques known in the art. Consequently, the sensitivity or LLOQ is increased by at least about 5-fold, at least about 10-fold, at least about 20-fold, at least about 50-fold or at least about 100-fold in comparison with techniques known in the art. Similarly, present invention provides for a cell line and ultimately use thereof in a kit for an increased dynamic range which is at least about 10-fold in comparison with techniques known in the art. Consequently, the dynamic range is at least about 5-fold, at least about 10-fold, at least about 20-fold, at least about 50-fold or at least about 100-fold in comparison with techniques known in the art. Examples of techniques known in the art may be found in Bhavin S. Parekh, B. S., et al. mAbs, 2012, 4(3), pp. 310-318, or e.g. Cheng, Z. J., et al., J. Immunol. Methods, 2014, 414, pp. 69-81.

The invention relates to a cell. In particular, the invention relates to a cell comprising one or more vectors according to the invention. The vectors may be episomal or integrated in the genome of said cell. The cell may be of any origin and in particular a mammalian cell. The cells according to the invention may be of any cell line known in the art such as e.g. Jurkat, Molt4, Raji, SKBR3, NK92, KHYG-1, HEK293, DT-40 and MSB-1. The present invention relates to overexpression in a cell of one or more co-stimulatory molecules that will result in an enhanced dynamic range and increased sensitivity when said cells are used to assess the ADCC or ADCP activity of an antibody. The co-stimulatory molecules may act as ligands when expressed endogenously or overexpressed on a target cell that carries a specific antigen recognized by the antibody. In one embodiment of the invention the target cell has been engineered to over-express a constant high level of a specific antigen recognized by a therapeutic antibody as disclosed in WO 2018/065401. The co-stimulatory molecules may act as co-stimulatory receptors when expressed endogenously or over-expressed on an effector cell. In one embodiment of the invention the effector cell has been engineered to over-express either the low affinity Fc receptor, FcγRIIIa (CD16A) V or F variants, or FcγRIIa (CD32) H or R variants that respond to ligation of the Fc moiety of antibody bound to the specific antigen expressed on target cells by activation of a NFAT responsive reporter gene as described previously (1,2), or by activation of a novel synthetic chimeric promoter containing binding sites for NF-AT, AP1, NFkB, and STAT5 operationally linked to the firefly luciferase (FL) reporter-gene as disclosed in WO 2018/065401.

In another aspect of the invention the effector cell has been engineered to over-express e.g. either the high affinity Fc receptor, FcγRI (CD64), or e.g. the low affinity Fc inhibitory receptor FcγRIIB1 (CD32), or the low affinity Fc inhibitory receptor FcγRIIB2 (CD32), or the low affinity Fc receptor FcγRIIIB (CD16b) that respond to ligation of the Fc moiety of antibody bound to the specific antigen expressed on target cells by activation of a NFAT responsive reporter gene as described previously (1,2), or by activation of a novel synthetic chimeric promoter containing binding sites for NF-AT, AP1, NFkB, and STAT5 operationally linked to the firefly luciferase (FL) reporter-gene as disclosed in WO 2018/065401.

The co-stimulatory molecules over-expressed on a target cell will interact with the co-stimulatory receptor(s), expressed endogenously or over-expressed, on the effector cell and potentiate the interaction of the Fc moiety of an antibody with the FcγIIIa or FcγII receptors on the effector cell resulting in a markedly enhanced expression of the FcγIIIa or FcγII receptor linked reporter-gene. This has for consequence a marked increase in the dynamic range and sensitivity of an ADCC or ADCP assay using effector cells expressing a FcγIIIa receptor responsive reporter-gene respectively as disclosed in WO 2018/065401, or effector cells expressing a FcγII responsive reporter gene as described herein or available commercially respectively with said target cells expressing one or more co-stimulatory molecules including CD80 (B7.1), CD86 (B7.2), and CD137 (4-1BB) in addition to the specific antigen recognized by the antibody.

It is understood that other co-stimulatory molecules such as ICOS-L (Inducible Co-stimulator Ligand), may also be expressed on the target cells to potentiate either FcγIIIa or FcγII receptor linked reporter-gene expression in an ADCC or ADCP assay respectively following its interaction with the ICOS receptor, expressed endogenously or over-expressed on the effector cells. In a further embodiment of the invention immune checkpoint receptors such as CTLA-4 (CD152) are specifically invalidated on effector cells using genome editing in order to prevent downregulation of CD80 and CD86 on target cells. In a further embodiment of the invention the CD3 zeta chain transmembrane signaling molecule (CD247) is over-expressed in the ADCC effector cells in order to potentiate FcγRIIIa associated immunoreceptor tyrosine activation motif (ITAM) signaling and enhanced expression of the FcγIIIa receptor linked reporter-gene.

In one aspect, the invention relates to a cell which may be denoted as an effector cell, wherein one or more of CD28, CD137 (4-1BB), CD247 (T3 Zeta chain), or CD278 (ICOS) are either expressed constitutively or over-expressed on the effector cells.

In another aspect, the invention relates to a cell which may be denoted as a target cell, wherein one or more of CD80, CD86, CD137L, and/or CD278L are either expressed constitutively or over-expressed on the target cells.

The invention also relates to a kit or a kit of parts. The kit may comprise:
i) a cell according to the invention that may act as an effector cell in an ADCC or ADCP mechanism and in which one or more co-stimulatory molecules are expressed endogenously or over-expressed,
ii) a cell according to the invention that may act as a target cell in an ADCC or ADCP mechanism in which the expression of one or more co-stimulatory molecules is enhanced,
iii) a target cell in which the endogenous target to which an antibody is specific is invalidated (mutated).

The kit also comprises a target cell wherein the same target is enhanced, i.e. such that the target is overexpressed as disclosed in WO 2018/065401 and in which the expression of one or more co-stimulatory molecules is enhanced.

The target may in principle be any target to which the relevant antibody can bind. In one aspect the target may be one or more of CD20, mTNFα, erbB2, EGFR.

The kit may also comprise one or more vials, such as e.g. 2 or more vials etc. In one aspect, the kit may comprise one vial which comprises a mixture of cells i) with a mixture of cells ii). In such instance the kit comprises two vials, the second vial comprises the cells of iii) as mentioned above. Thus, in one instance, the kit comprises two vials wherein one vial comprises the effector cells i) and the target cells ii) having the target to which the antibody in question is specific enhanced/overexpressed. The second vial consequently comprises the target cells iii), wherein the target is invalidated or target/receptor is deleted or otherwise may non-functional or has by any means lost its capability to bind the antibody in question.

In one aspect of the invention, one vial of the kit comprises a mixture of cells i) with a mixture of cells ii) in an optimal ratio referred herein as the E:T ratio, wherein E denotes the cells in paragraph i) above (Effector cells). T denotes the cells in iii) above (Target cells). The optimal E:T ratio is further described herein and in the experimental part.

In the kit and the method according to the invention the same E:T ratio is used for the effector cells i) and the target cells iii), as has been found for the relation between effector cells i) and target cells ii).

DETAILED DESCRIPTION OF THE INVENTION

These features are obtained by means of the present invention in which recombinant effector cells expressing CD16A (V or F variant) functionally linked to the firefly luciferase reporter gene as disclosed in WO 2018/065401, or effector cells expressing CD32 (H or R variant) functionally linked to the firefly luciferase reporter gene as described herein, or effector cells engineered to over-express either the high affinity Fc receptor, FcγRI (CD64), or the low affinity Fc inhibitory receptor FcγRIIB1 (CD32), or the low affinity Fc inhibitory receptor FcγRIIB2 (CD32), or the low affinity Fc receptor FcγRIIIB (CD16b) functionally linked to the firefly luciferase reporter gene as disclosed in WO 2018/065401, or to the firefly luciferase reporter gene as described herein or effector cells expressing CD16A or CD32 functionally linked to NFAT-responsive reporter-gene as available commercially, that express endogenously or over-express one or more co-stimulatory receptors including CD28, CD137 (4-1BB), and ICOS, are used in conjunction with target cells expressing an antigen recognized specifically by an antibody and over-expressing one or more co-stimulatory molecules including CD80, CD86, CD132L, or ICOSL result in an enhanced dynamic range and increased sensitivity when said cells are used to assess the ADCC or ADCP activity of an antibody.

Consequently, the invention relates to a polynucleotide comprising a cis-acting regulatory sequence operably linked to a downstream promotor, wherein one or more of NF-AT, AP1, NFkB, STAT1, STAT3 and STAT5 are capable of binding to said cis-acting regulatory sequence. In one aspect of the invention NF-AT, AP1, NFkB, and STAT5 are all capable of binding to said cis-acting regulatory sequence.

The promotor may be operable linked to an open read frame sequence encoding a first reporter protein, such as e.g. an enzyme which may be a luciferase or a fluorescent protein.

The polynucleotide according to the invention may comprise or consist of a nucleotide sequence having at least about 70% sequence identity, such as e.g. at least about 75% sequence identity, such as e.g. at least about 80% sequence identity, such as e.g. at least about 85% sequence identity, such as e.g. at least about 90% sequence identity, such as e.g. at least about 95% sequence identity, such as e.g. at least about 98% sequence identity, such as e.g. at least about 99% sequence identity to SEQ ID NO.: 1 or a DNA sequence identical to SEQ ID NO.: 1, wherein SEQ ID NO.: 1 is;

```
GGAAGCGAAA ATGAAATTGA CTGGGACTTT CCGGAGGAAA

AACTGTTTCA TACAGAAGGC GTGGATGTCC ATATTAGGAT

GAGTCAGTGA CGTCAGAGCC TGATTTCCCC GAAATGATGA

GCTAG.
```

In one aspect, the polynucleotide according to the invention is an artificial, engineered polynucleotide.

In one aspect, the polynucleotide according to the invention may comprise or consist of a nucleotide sequence having at least about 90% sequence identity, such as e.g. at least about 95% sequence identity, such as e.g. at least about 98% sequence identity, such as e.g, at least about 99% sequence identity to SEQ ID NO.: 1 or a DNA sequence identical to SEQ ID NO.: 1.

In a further aspect, the polynucleotide according to the invention may comprise or consist of a nucleotide sequence having at least about 95% sequence identity, such as e.g. at least about 96% sequence identity, such as e.g. at least about 97% sequence identity, such as e.g. at least about 98% sequence identity, such as e.g. at least about 99% sequence identity to SEQ ID NO.: 1 or a DNA sequence identical to SEQ ID NO.: 1.

The invention also relates to a vector construct comprising the polynucleotide according to the invention. The vector construct may be a plasmid or viral vector.

In one aspect of the invention, the vector construct may comprise the polynucleotide sequence as set forth in SEQ ID NO.: 1, and further comprising one or more nucleotide sequences capable of encoding proteins for expression of one or more co-stimulatory molecules as disclosed herein.

The vector construct thus may comprise a polynucleotide which may comprise or consist of a nucleotide sequence having at least about 70% sequence identity, such as e.g. at least about 75% sequence identity, such as e.g. at least about 80% sequence identity, such as e.g. at least about 85% sequence identity, such as e.g. at least about 90% sequence identity, such as e.g. at least about 95% sequence identity, such as e.g. at least about 98% sequence identity, such as e.g. at least about 99% sequence identity to SEQ ID NO.: 1 or a DNA sequence identical to SEQ ID NO.: 1, wherein SEQ ID NO.: 1 is;

```
GGAAGCGAAA ATGAAATTGA CTGGGACTTT CCGGAGGAAA

AACTGTTTCA TACAGAAGGC GTGGATGTCC ATATTAGGAT

GAGTCAGTGA CGTCAGAGCC TGATTTCCCC GAAATGATGA

GCTAG.
```

In one aspect, the vector construct may comprise a polynucleotide that may comprise or consist of a nucleotide sequence having at least about 90% sequence identity, such as e.g. at least about 95% sequence identity, such as e.g. at least about 98% sequence identity, such as e.g. at least about 99% sequence identity to SEQ ID NO.: 1 or a DNA sequence identical to SEQ ID NO.: 1.

In a further aspect, the vector construct may comprise a polynucleotide that may comprise or consist of a nucleotide sequence having at least about 95% sequence identity, such as e.g. at least about 96% sequence identity, such as e.g. at least about 97% sequence identity, such as e.g. at least about 98% sequence identity, such as e.g. at least about 99% sequence identity to SEQ ID NO.: 1 or a DNA sequence identical to SEQ ID NO.: 1.

Moreover, the invention also relates to a cell comprising the vector according to the invention. Specifically, present invention relates to an engineered cell comprising the vector according to the invention. The vector may be episomal or integrated in the genome of said cell. In one aspect of the invention the cell may further express a second reporter protein which different from the first reporter protein. In yet a further aspect of the invention, the cell may be recombinant.

In one aspect of the invention, the cell comprising the vector with the polynucleotide (SEQ ID NO.: 1) as set forth herein may be the effector cell. As previously mentioned, the vector or vector construct may comprise a polynucleotide which may comprise or consist of a nucleotide sequence having at least about 70% sequence identity, such as e.g. at least about 75% sequence identity, such as e.g. at least about 80% sequence identity, such as e.g. at least about 85% sequence identity, such as e.g. at least about 90% sequence identity, such as e.g. at least about 95% sequence identity, such as e.g. at least about 98% sequence identity, such as e,g, at least about 99% sequence identity to SEQ ID NO.: 1 or a DNA sequence identical to SEQ ID NO.: 1, wherein SEQ ID NO.: 1 is;

```
GGAAGCGAAA ATGAAATTGA CTGGGACTTT CCGGAGGAAA

AACTGTTTCA TACAGAAGGC GTGGATGTCC ATATTAGGAT

GAGTCAGTGA CGTCAGAGCC TGATTTCCCC GAAATGATGA

GCTAG.
```

In one aspect, the vector construct may comprise a polynucleotide that may comprise or consist of a nucleotide sequence having at least about 90% sequence identity, such as e.g. at least about 95% sequence identity, such as e.g. at least about 98% sequence identity, such as e.g. at least about 99% sequence identity to SEQ ID NO.: 1 or a DNA sequence identical to SEQ ID NO.: 1.

In a further aspect, the vector construct may comprise a polynucleotide that may comprise or consist of a nucleotide sequence having at least about 95% sequence identity, such as e.g. at least about 96% sequence identity, such as e.g. at least about 97% sequence identity, such as e.g. at least about 98% sequence identity, such as e.g. at least about 99% sequence identity to SEQ ID NO.: 1 or a DNA sequence identical to SEQ ID NO.: 1.

In one aspect of the invention, the cell comprising the vector with the polynucleotide (SEQ ID NO.: 1) as set forth herein may be the effector cell, and wherein the vector further comprises one or more nucleotide sequences capable of encoding proteins for expression of one or more co-stimulatory molecules as disclosed herein. Exemplary and non-limiting examples are one or more of CD28, CD137 (4-1BB), CD247 (T3 Zeta chain), or CD278 (ICOS) which may either be expressed constitutively or over-expressed on the effector cells (e.g. on the cell surface).

Thus, in one aspect of the invention, the cells are effector cells may express CD16A functionally linked to the reporter gene, such as e.g. the gene expressing an enzyme which may be a luciferase or a fluorescent protein.

Alternatively, the cells according to the invention are effector cells may express CD32 functionally linked to the reporter gene, such as e.g. the gene expressing an enzyme which may be a luciferase or a fluorescent protein.

In one aspect of the invention, the cells effector cells according to the invention further express endogenously or over-express one or more co-stimulatory receptors. In principle such co-stimulatory receptors may be any suitable receptor and may be e.g. one or more of CD28, CD137 (4-1BB), and ICOS. Moreover, one or more of CD28, CD137 (4-1BB), CD247 (T3 Zeta chain), or CD278 (ICOS) may be either expressed constitutively or over-expressed on the effector cells.

The invention also relates to target cells. Moreover, the target cells express an antigen specifically recognized by an antibody. In one aspect of the invention, the target cells over-express one or more co-stimulatory molecules such as e.g. one or more of CD80, CD86, CD132L, CD137L, or ICOSL. Moreover, one or more of CD80, CD86, CD137L, and/or CD278L may be either expressed constitutively or over-expressed on the target cells.

In a further embodiment of the invention immune checkpoint receptors such as CTLA-4 (CD152) are specifically invalidated on effector cells using genome editing in order to prevent CD28 downregulation and in turn negation of the effect of over-expression of CD80 and CD86 on target cells. In a further embodiment of the invention the trans-membrane CD3 associated zeta signaling molecule (CD247) containing three immuno-receptor tyrosine activation motifs (ITAM) is over-expressed in the ADCC effector cells in order to potentiate FcγRIIIa associated ITAM signaling and enhanced expression of the FcγIIIa receptor linked reporter-gene. In a preferred embodiment, in order to provide for a normalization of the assay, the recombinant effector cells further have a construct for the constitutive production of a luciferase that is different from that used in the reporter gene construct. For example, when the reporter gene construct produces firefly luciferase, the constitutive production may be of a second luciferase, e.g., *Renilla* luciferase (4). The activity of the first luciferase normalized relative to the activity of the second luciferase is described in US 2011/0189658 incorporated herein in its entirety by reference. When conducting the assay, after the reporter gene luciferase is measured, then a reagent is added to quench that specific luciferase so that any following reading will just read the luciferase from the constitutive construct, which then may be used for the purpose of normalization, as will be described in more detail in the examples.

The advantages of using the constitutive expression of any luciferase is that the results are not influenced by loss of effector cells or by target cell killing of effector cells, nor are the results influenced by serum matrix effects. All of these can be compensated for by the normalization obtained through the use of the measurement of the constitutive expression of the other (second) luciferase. None of these advantages can be obtained in the procedure of prior art assays which does not use such normalization.

In a preferred embodiment of the present invention, target cells are produced from the same type of target cell as is being measured in vivo but with the antigen to which the antibody is specific being invalidated on the one hand (negative control) or its expression being enhanced in a constant manner on the other (positive control) as disclosed in WO 2018/065401. Prior art assays use only wild type target cells that express variable amounts of the antigen to which the antibody is specific, not recombinant, for the positive control, and natural cells that do not constitutively express the antigen to which the antibody is specific, for the negative control. For example, in the CD20 assay, T cells are used which do not constitutively express CD20 as the negative control. For the positive control, wild type B-cells are used as the target.

By using a recombinant target cell in which the antigen to which the antibody is-specific has been invalidated, one has a much improved negative control as T cells are very different from the natural target cell and these differences affect the results somewhat. For example, it can prevent the heterologous effector cell (E) target cell (T) ratio (E:T ratio) curve from being a completely zero as the number of target cells is increased as the E:T ratio is changed. This problem is solved by using a recombinant target cell in which the gene, encoding the specific antigen recognized by the monoclonal antibody, has been invalidated.

A further preferred feature of the present invention recombinant target cells that have an enhanced constant expression of the antigen to which the antibody is specific as disclosed in WO 2018/065401, are co-transfected with one or more co-stimulatory molecules such as CD80 or CD86 thereby allowing a much greater dynamic range and enhanced sensitivity to be obtained for an ADCC or ADCP assay.

Furthermore, the co-stimulatory molecules CD80 & CD86 and the specific antigen are expressed at constant high levels that do not vary as cells proliferate or as a function of culture conditions as is the case for the wild type cells therefore affording improved assay precision. This allows the detection of subtle differences in ADCC or ADCP activity of candidate antibodies to be determined. Another advantage of the recombinant target cells is that they can be provided in freeze, thaw and use format for much greater ease of use than either the harvesting or cultivation of target cells from human subjects or cultivation of target cell lines in the laboratory. Using such recombinant cells avoids the variability that will inherently be present in the target cells obtained from normal individuals or cells cultivated in vitro as such wild type cells will have variable expression of the antigen of interest depending on stage of maturation, the phase of the cell cycle or culture conditions. The use of a recombinant positive control eliminates this variability.

A further preferred feature of the present invention is a thaw and use format comprising vials of effector cells and vials of target cells frozen separately using standard techniques. Upon thawing, effector cells and target cells are mixed at the optimal E:T ratio and incubated for the appropriate time in a multi-well white-sided microtiter plate in the presence of increasing concentrations of the antibody to be analyzed. Antibody induced firefly luciferase (FL) activity and the constitutive *Renilla* luciferase (RL) expression are then quantified sequentially in the same well of a microtiter plate in a luminometer using a dual luciferase substrate. Results are expressed as relative luciferase units (RLU) and presented as in the form of a 4-parametric logistic (4PL) plot as shown in the following examples.

A further preferred feature of the present invention is a single frozen vial containing both effector cells and target cells at the optimal E:T ratio for a particular monoclonal antibody such as rituximab such that all the customer has to do is to add drug at a desired concentration, incubate and take a reading. A single frozen vial containing both effector cells and negative control target cells at the optimal E:T ratio for a particular monoclonal antibody is also supplied. Consequently, according to the invention the E:T ratio is in range from about 24:1 to about 1:1. Preferably, the ratio is e.g. about 24:1 to about 2:1, or about 6:1, or about 3:1, or about e.g. 1.5:1, or about 1:1. Such a format obviates the necessity for the user of the kit or method to determine the optimal E:T ratio and other assay parameters for a particular monoclonal antibody.

In a further embodiment of the present invention in order to facilitate the quantification of the ADCC or ADCP activity of antibodies that are directed to CD20, the co-stimulatory molecules CD80 and or CD86 are over-expressed in cells that express CD20. In a preferred embodiment of the present invention the co-stimulatory molecules CD80, CD86 or CD80 and CD86 are over-expressed in target cells that express a constant high level of CD20 expression such as those disclosed in WO 2018/065401.

In a further embodiment of the present invention in order to facilitate the quantification of the ADCC or ADCP activity of antibodies that are directed to the HER2 receptor, the co-stimulatory molecules CD80, CD86 or CD80 and CD86 are over-expressed in cells that express ERBB2. In a preferred embodiment of the present invention the co-stimulatory molecules CD80, CD86, or CD80 and CD86 are over-expressed in target cells that express a constant high level of ERBB2 expression such as those disclosed in WO 2018/065401.

In a further embodiment of the present invention in order to facilitate the quantification of the ADCC or ADCP activity of antibodies that are directed to the EGFR receptor, the co-stimulatory molecules CD80, CD86, or CD80 and CD86 are over-expressed in cells that express EGFR. In a preferred embodiment of the present invention the co-stimulatory molecules CD80, CD86 or CD80 and CD86 are over-expressed in target cells that express a constant high level of EGFR expression such as those disclosed in WO 2018/065401.

In a further embodiment of the present invention to facilitate the quantification of the ADCC activity of infliximab or any other anti-TNF-α antibody or Fc fusion protein such as e.g. etanercept (Enbrel®), the co-stimulatory molecules CD80, CD86, or CD80 and CD86 are over-expressed on target cells such as those disclosed in WO 2018/065401 that express membrane bound TNFα (mTNFα) since the quantification of the ADCC activity of TNFα antagonists requires a target cell expressing membrane bound TNFα. Although TNFα is initially membrane bound it is subsequently cleaved by ADAM17 (TACE) protease. Thus, in order to establish a cell line that expresses membrane-bound non-cleavable TNFα site-directed mutagenesis was used to mutate the protease cleavage site. Non-cleavable TNFα expressed on the surface of a cell will bind, however, to the TNFαRII receptor present on the surface of neighboring cells resulting in cell death and rendering the establishment of a permanent cell line difficult. Thus, or order to obviate such difficulties the TNFαRII receptor was invalidated using genome editing and in the negative control TNFα expression was invalidated using genome editing but not the TNFαRII receptor as disclosed in WO 2018/065401.

In one aspect, present invention relates to use of SEQ ID NO.:1 in an engineered cell.

In another aspect, present invention relates to use of a cell according to the invention as disclosed herein, in a biological assay.

In yet a further aspect, the invention relates to use of a cell according to the invention as disclosed herein, in diagnostics or a diagnostic method.

Present invention also relates to use of a cell according to the invention in an assay for enhanced dynamic range and/or increased sensitivity in the assay.

In one aspect, the invention relates to use of a cell according to the invention in an assay for enhanced dynamic range and/or increased sensitivity in the assay, wherein said cells are used to assess the ADCC and/or ADCP activity of an antibody.

Definitions

The terms "invalidated" or "muted" used interchangeably herein is meant to knock out a particular gene to ultimately change the phenotype of a cell. Effectively, the term is meant to encompass rendering a gene non-functional. An example may be the invalidation of a certain gene to remove the expression of a surface cell receptor.

The term "++" in relation to a "++ cell" is intended to mean a target cell in which the antigen (drug target) is overexpressed. The terminology is used interchangeably herein with "T+". Moreover, when the expression is used together with a receptor or antigen such as e.g. $CD20^{++}$ is intended to mean that CD20 is overexpressed on the cell in question. As an example without intending to limit the scope of the invention, in the case of CD20 expression levels are increased some 16-fold on $CD20^{++}$ target cells relative to the wild type $CD20^+$ Raji cells as disclosed in WO 2018/065401.

The terms erbB2 and ERBB2 are interchangeable and denote the antigen recognized by e.g. transtuzumab.

The term "−/−" in relation to "−/− cell" is intended to mean a target cell in which the antigen (drug target) is not expressed, i.e. wherein the relevant gene has been knocked-out (invalidated) to mute the expression of the antigen/receptor in question. The terminology is used interchangeably herein with "T−". Consequently, the cells no longer express detectable levels of the specific antigen recognized by the antibody since the gene encoding the specific antigen has been rendered nonfunctional. In the context of present invention this may be seen as a control target cell.

The term "E" is intended to mean "effector cells" and particularly effector cells according to the invention. The term "effector cell" is intended to mean any cell of any type that actively responds to a stimulus and effects some change (brings it about). One such example is cytokine-induced killer cells, strongly productive cytotoxic effector cells that are capable of lysing tumor cells. In a further example and in the context of present invention an effector cell is intended to mean any cell having Fc gamma receptors (FcγR or FCGR) on the surface of said cell which bind the Fc region of an antibody, wherein the antibody itself is specifically capable of binding to a target cell.

The term "T" is intended to mean a "target cell", i.e. any cell having a specific receptor/antigen that reacts with a specific hormone, antigen, antibody, antibiotic, sensitized T cell, or other substance. In relation thereto the term "(T+)" is intended to mean antigen positive target cells and consequently a cell expressing an antigen on its surface and allowing for binding of an antibody. In contrast, the term "(T−)" is intended to mean an antigen negative target cells (control target cell) and consequently a cell not expressing an antigen on its surface and thus not capable of reacting with an antibody. Put differently, antigen −/− cells (or T− cells) do not express detectable levels of the specific antigen recognized by the antibody that is being tested for ADCC activity since the gene encoding the specific antigen has been rendered nonfunctional. Specifically, the target cells used according to the invention are the same type of cells which is in contrast to known methods which usually employ one cell type as the T+ cell and employs another cells type as the T− cell. Put differently, a homologous control target cells that is exactly the same cell identical in all respects as the antigen positive target (T+) cell except that it does not express the specific antigen recognized by the antibody being assayed. As mentioned above, this is in contrast to the use of a T-cell (T lymphocyte), for example, that is often used as a control target cell for the quantification of ritiximab activity using a CD20 expressing B-cell target cells

EXAMPLES

Example 1: Establishment of an Engineered CD16 Responsive Effector Cell Line Overexpressing the Co-Stimulatory Receptor CD28

Jurkat cells (ATCC® TIB-152) expressing either the V-variant or F-variant of CD16A functionally linked to the firefly luciferase (FL) reporter gene regulated by a novel synthetic chimeric promoter containing binding sites for NF-AT, AP1, NFkB, and
STAT5 previously disclosed in WO 2018/065401 were transfected with the gene encoding the co-stimulatory receptor CD28 using the FuGENE HD transfection reagent (Promega Catalogue N° E2311). Positive clones were enriched using fluorescent activated cell sorting and an anti-CD28 monoclonal antibody (ImmunoTools, Catalogue N° 21270280) together with a FITC goat anti-mouse IgG (ImmunoTools, Catalogue N° 22549913). The cells were also transfected with the gene encoding *Renilla* luciferase (RL) under the control of a constitutive promoter that allows ADCC activated FL activity to be normalized relative to the constitutive expression of RL activity rendering results independent of cell concentration. Stable clones were isolated and characterized for ADCC activity in the presence of the ADCC target cells over-expressing CD20 previously disclosed in WO 2018/065401 and rituximab and then sub-cloned. A stable sub-clone was isolated and shown to express an enhanced FL signal when used to assess the ADCC activity of an antibody in conjunction with recombinant target cells expressing an antigen recognized specifically by an antibody and over-expressing one or more co-stimulatory molecules including CD80 and or CD86 as illustrated in the following examples.

Example 2: Establishment of an Engineered CD16 Responsive Effector Cell Line Overexpressing the Co-Stimulatory Receptor CD137 (4-1BB)

Jurkat cells (ATCC® TIB-152) expressing either the V-variant or F-variant of CD16A functionally linked to the firefly luciferase (FL) reporter gene regulated by a novel synthetic chimeric promoter containing binding sites for NF-AT, AP1, NFkB, and STAT5 previously disclosed in WO 2018/065401 were transfected with the gene encoding the co-stimulatory receptor CD137 (4-1BB) using the FuGENE HD transfection reagent (Promega Catalogue N° E2311). The results of a series of transient transfection experiments show that expression of CD137 in Jurkat effector cells expressing the FcγRIIIA receptor functionally linked to the FL reporter gene regulated by a novel synthetic chimeric promoter containing binding sites for NF-AT, AP1, NFkB, and STAT5 previously disclosed in WO 2018/065401 when used in conjunction with HEK293 target cells over-expressing ERBB2 and one or more co-stimulatory molecules markedly increased the FL signal of an ADCC assay using trastuzumab (FIG. 1A). Following stable transfection of the effector cells disclosed in WO 2018/065401 with the gene encoding CD137 positive clones were enriched using fluorescent activated cell sorting and an Alexa-488 conjugated anti-CD137 monoclonal antibody (R & D Systems Catalogue N° FAB838G). The cells were also transfected with the gene encoding *Renilla* luciferase (RL) under the control of a constitutive promoter that allows ADCC activated FL activity to be normalized relative to the constitutive expression of RL activity rendering results independent of cell concentration. Stable clones were isolated and characterized for ADCC activity in the presence of the ADCC target cells over-expressing ERBB2 previously disclosed in WO 2018/065401 and trastuzumab and then sub-cloned. A stable sub-clone was isolated and shown to express an enhanced FL signal when used to assess the ADCC activity of an antibody in conjunction with recombinant target cells expressing an antigen recognized specifically by an antibody and over-expressing one or more co-stimulatory molecules including CD80 and or CD86 as illustrated in the following examples.

Example 3: Establishment of an Engineered CD16A Responsive Effector Cell Lines Overexpressing the Zeta Signaling Chain Alone or Together with the Co-Stimulatory Receptor CD28

Figure 1B:
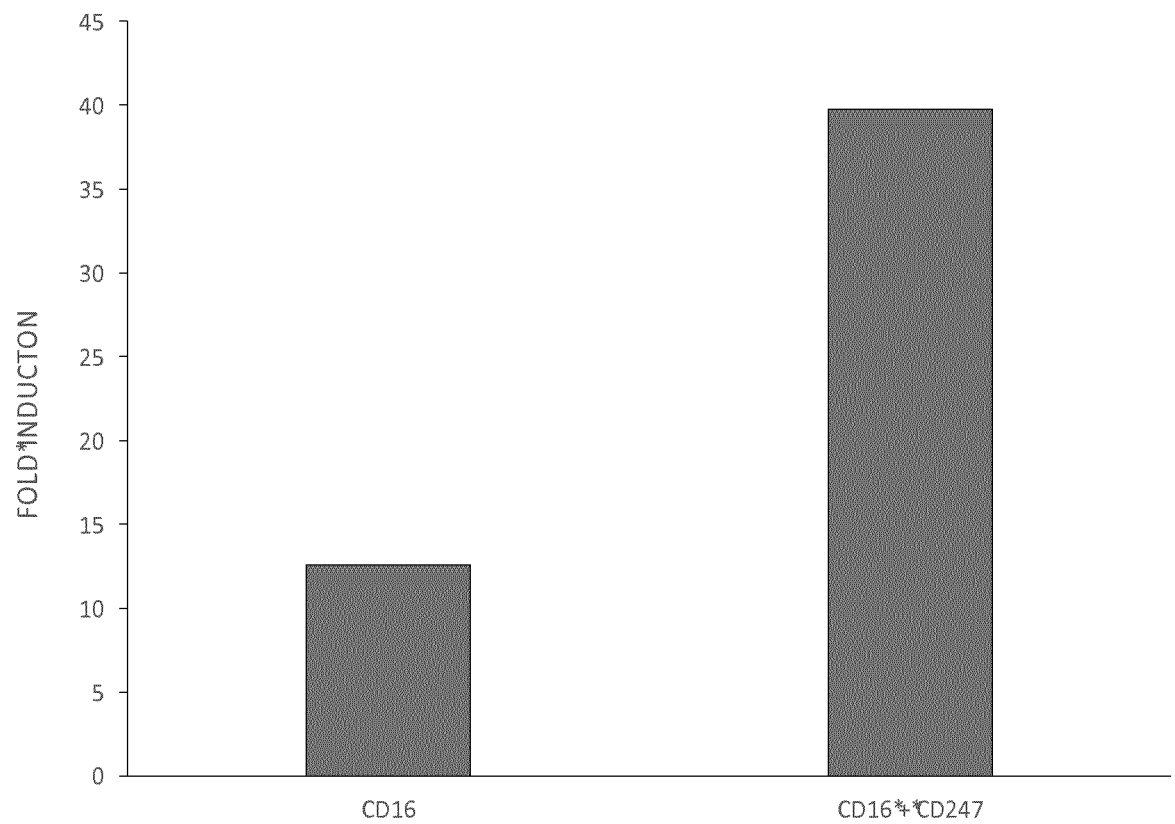
FIG. 1B illustrates a comparison of the ADCC activity of rituximab determined using the iLite® effector cells (V-variant) co-transfected or not with the zeta transmembrane signaling molecule associated with CD3 and Raji target cells over-expressing CD20.

In order to optimize ITAM signaling from the FcγRIIIA receptor and hence increase the dynamic range and sensitivity of an ADCC assay Jurkat effector cells expressing the FcγRIIIA receptor functionally linked to the FL reporter gene regulated by a novel synthetic chimeric promoter containing binding sites for NF-AT, AP1, NFkB, and STAT5 previously disclosed in WO 2018/065401, or the effector cells over-expressing CD28 described in Example 1, were transfected with the trans-membrane zeta signaling molecule (CD247) associated with CD3 that contains three ITAM activation motifs (4) using the FuGENE HD transfection reagent (Promega Catalogue N° E2311). The results of a series of transient transfection experiments show that overexpression of the zeta transmembrane signaling molecule alone (FIG. 1B), or together with CD28 in Jurkat effector cells expressing the FcγRIIIA receptor functionally linked to the FL reporter gene regulated by a novel synthetic chimeric promoter containing binding sites for NF-AT, AP1, NFkB, and STAT5 previously disclosed in WO 2018/065401 when used in conjunction with HEK293 target cells over-expressing ERBB2 alone or together with CD86 markedly increased the FL signal of an ADCC assay using trastuzumab (FIG. 1B). Following stable transfection of the effector cells disclosed in WO 2018/065401 with the trans-membrane zeta signaling molecule (CD247) using the FuGENE HD transfection reagent (Promega Catalogue N° E2311) positive clones were enriched using fluorescent activated cell sorting and FITC labelled anti-CD247 monoclonal antibody (AbCam, Catalogue N° H46-968). The cells were also transfected with the gene encoding *Renilla* luciferase under the control of a constitutive promoter that allows ADCC activated FL activity to be normalized relative to the constitutive expression of RL activity rendering results independent of cell concentration. Stable clones were isolated and characterized for ADCC activity in the presence of the ADCC target cells over-expressing ERBB2 previously disclosed in WO 2018/065401 and trastuzumab and then sub-cloned. The use of said cells resulted in an enhanced FL signal, dynamic range, and sensitivity, when use to assess the ADCC activity of an antibody in conjunction with recombinant target cells expressing an antigen recognized specifically by an antibody and over-expressing one or more co-stimulatory molecules including CD80 and or CD86.

Example 4: Establishment of an Engineered CD32 Responsive Effector Cell Line

In order to optimize signaling from the FcγRIIA receptor and hence the dynamic range and sensitivity of an ADCP assay Jurkat cells were transfected with the FcγRIIA receptor functionally linked to the FL reporter gene regulated by a novel synthetic chimeric promoter containing binding sites for NF-AT, AP1, NFkB, and STAT5 previously disclosed in WO 2018/065401 using the FuGENE HD transfection reagent (Promega Catalogue N° E2311). Positive clones were enriched using fluorescent activated cell sorting and FITC labelled anti-CD32 monoclonal antibody (AbCam, catalogue N° ab30356). The cells were also transfected with the gene encoding *Renilla* luciferase (RL) under the control of a constitutive promoter that allows ADCP activated FL activity to be normalized relative to the constitutive expression of RL activity rendering results independent of cell concentration. Stable clones were isolated and characterized for ADCP activity in the presence of target cells over-expressing CD20 previously disclosed in WO 2018/065401 and rituximab. The use of said effector cells to assess the ADCP activity of an antibody in conjunction with recombinant target cells expressing an antigen recognized specifically by an antibody and over-expressing one or more co-stimulatory molecules including CD80 and or CD86 resulted in an ADCP assay with an enhanced signal, dynamic range and sensitivity relative to cells expressing FcγRIIA functionally linked to the FL reporter-gene under the control of a NFAT chimeric promoter as illustrated in the following examples.

Example 5: Establishment of an Engineered Target Cell Line Expressing High Constant Levels of CD20 and One or More Co-Stimulatory Molecules at the Cell Surface Raji cells (ATCC® CCL-86) over-expressing a constant high level of CD20 previously disclosed in WO 2018/065401 were transfected with the co-stimulatory molecule CD80, or CD86, or both CD80 and CD86 using the FuGENE HD transfection reagent (Promega Catalogue N° E2311). Positive clones were enriched using fluorescent activated cell sorting and phycerythrin labelled anti-CD80 (ImmunoTools, Catalogue N° 21270804) or FITC labelled anti-CD86 (ImmunoTools, Catalogue N° 21480863) monoclonal antibodies. Stable clones were isolated and characterized for ADCC activity in the presence of the ADCC effector cells previously disclosed in WO 2018/065401 and rituximab and then sub-cloned. Suitable sub-clones were isolated, characterized and propagated giving rise to $CD20^{++}$ target cell lines over-expressing CD80, or CD86 or both CD80 and CD86.

Figure 2A:
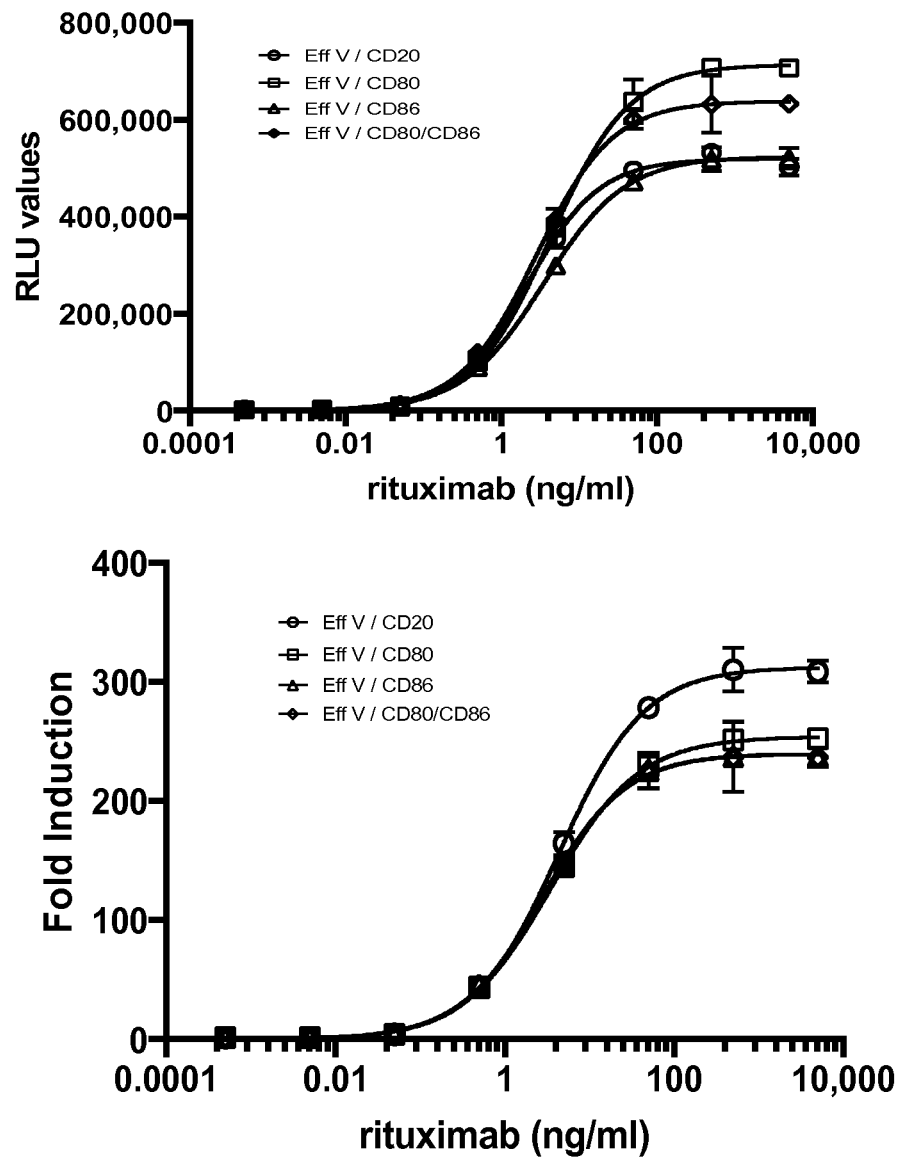
FIG. 2A illustrates a comparison of the ADCC activity of rituximab determined using the iLite® effector cells (V-variant) and Raji target cells over-expressing either CD20 alone or over-expressing both CD20 and the co-stimulatory molecules CD80, or CD86, or CD80 and CD86.

Vials of iLite® effector cells disclosed in WO 2018/065401 and vials of $CD20^{++}$ target cells over-expressing CD80, or CD86 or both CD80 and CD86 were frozen separately using standard techniques. Upon thawing, effector cells and target cells were mixed at E:T ratio of 3:1 and incubated for 4 hours in a 96-well white-sided microtiter plate (Perkin Elmer 6005181) in the presence of increasing concentrations of rituximab in RPMI 1640 culture medium+10% fetal bovine serum (FBS). FL activity was then determined using the Dual Glo (Promega 22920) dual luciferase substrate and light emission was quantified in a luminometer (GloMax, Promega) and expressed as relative luciferase units (RLU). Results are presented in the form of a 4-parametric logistic (4PL) plot as shown in FIG. 2A. The associated Table to FIG. 2A and Table 1 outline the principal parameters of a 4PL plot for the iLite® effector cells and a given target cell. When $CD20^{++}$ target cells over-expressing one or more co-stimulatory molecules were used to assess the ADCC activity of rituximab in conjunction with the ADCC V-variant effector cells previously disclosed in WO 2018/065401 the maximal FL signal of the ADCC assay was increased using target cells over-expressing CD80 although both the dynamic range and sensitivity were reduced relative to the use of target cells overexpressing CD20 alone. Similarly, overexpression of CD86 alone or together with CD86 reduced the dynamic range and sensitivity of an ADCC assay when used in in conjunction with the ADCC V-variant effector cells previously disclosed in WO 2018/065401 (FIG. 2A).

Figure 2B:
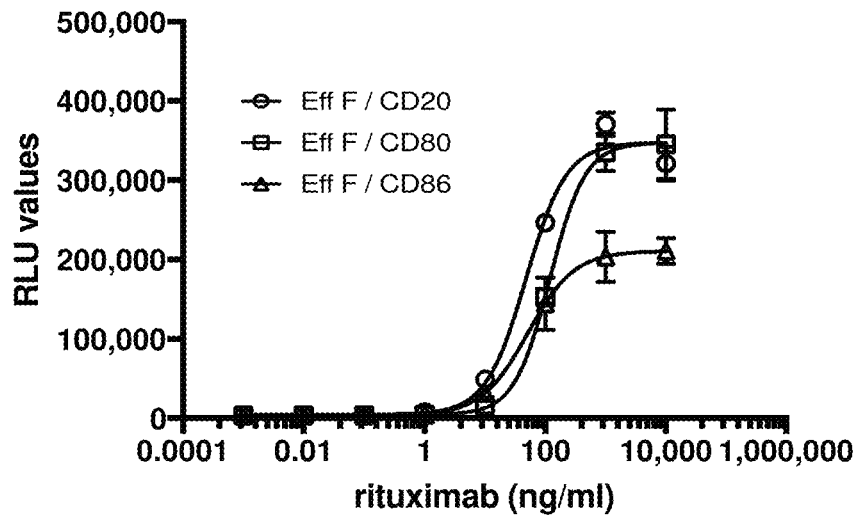
FIG. 2B illustrates a comparison of the ADCC activity of rituximab determined using the iLite® effector cells (F-variant) and Raji target cells over-expressing either CD20 alone or over-expressing both CD20 and the co-stimulatory molecules CD80, or CD86.
Figure 2B:
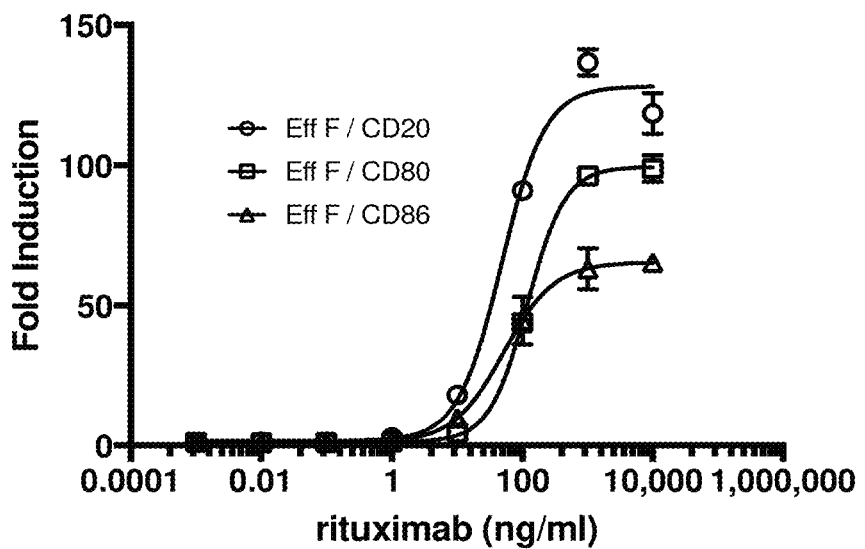

No increase in the maximal FL signal and a reduced dynamic range were observed when $CD20^{++}$ target cells over-expressing the co-stimulatory molecules CD80 or CD86 were used to assess the ADCC activity of rituximab in conjunction with effector cells expressing the F-variant of CD16A previously disclosed in WO 2018/065401 (FIG. 2B). Furthermore, the sensitivity of the assay was either not affected significantly or decreased (FIG. 2B).

The observation that overexpression of the co-stimulatory molecules CD80 and CD86 on Raji target cells overexpressing CD20 reduces the sensitivity and dynamic range of an assay to assess the ADCC activity of rituximab relative to an ADCC assay using Raji target cells overexpressing CD20 alone is most probably related to the high endogenous levels of expression of CD80 and CD86 on parental Raji cells (5) and increasing expression levels even further most probably induces CTLA-4 modulation of the effector cell CD28 target cells CD80-CD86 interaction (5).

Figure 3A:
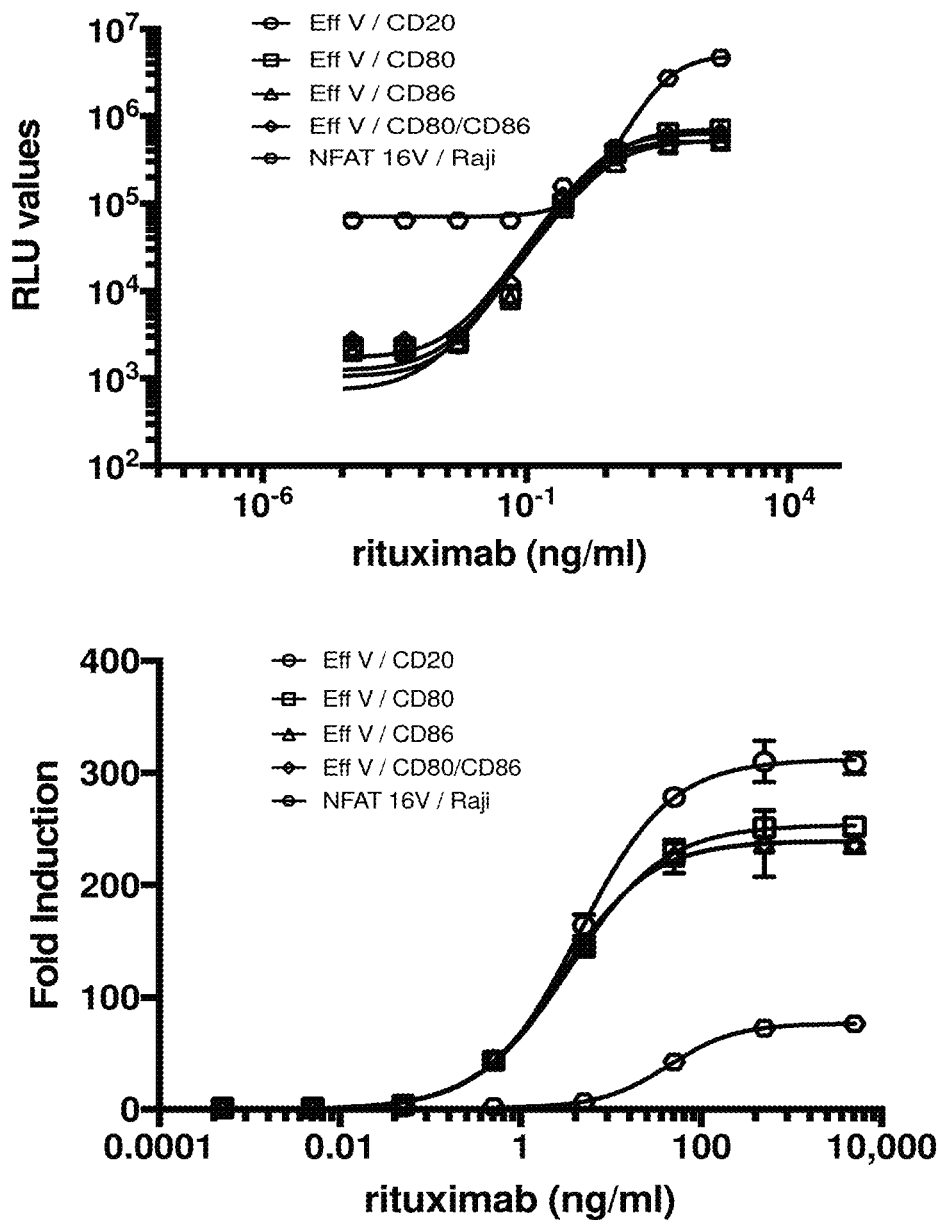
FIG. 3A illustrates a comparison of the ADCC activity of rituximab determined using the iLite® effector cells (V-variant) and Raji target cells over-expressing both CD20 and the co-stimulatory molecules CD80, or CD86, or CD80 and CD86 versus NFAT responsive effector cells (V-variant) and wild type Raji target cells.
Figure 3B:
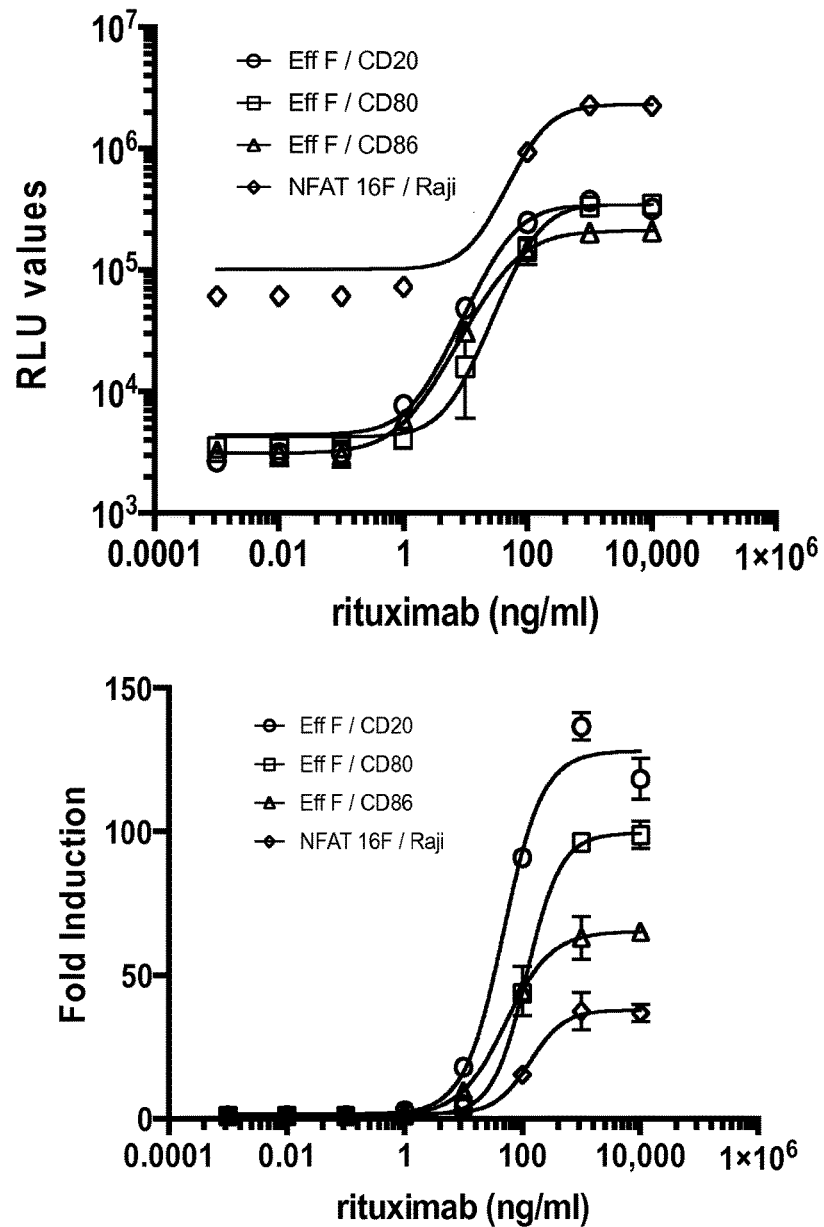
FIG. 3B illustrates a comparison of the ADCC activity of rituximab determined using the iLite® effector cells (F-variant) and Raji target cells over-expressing both CD20 and the co-stimulatory molecules CD80, or CD86 versus NFAT responsive effector cells (F-variant) and wild type Raji target cells.

Said Raji target cells over-expressing either CD20 alone or together with CD80, or CD86 or both CD80 and CD86 together when used to assess the ADCC activity of rituximab in conjunction with the ADCC V-variant effector cells previously disclosed in WO 2018/065401 resulted in an ADCC assay with a markedly enhanced dynamic range and sensitivity relative to an ADCC assay using NFAT responsive effector cells and wild type Raji target cells (FIG. 3A). The maximal FL signal was, however, lower that that observed with NFAT responsive effector cells and wild type Raji target cells (FIG. 3A). Although, no increase in the maximal FL signal and a reduced dynamic range and reduced sensitivity were observed when $CD20^{++}$ target cells over-expressing the co-stimulatory molecules CD80 or CD86 were used to assess the ADCC activity of rituximab in conjunction with effector cells expressing the F-variant of CD16A previously disclosed in WO 2018/065401 relative to that observed using CD20++ target cells alone (FIG. 3B) both the dynamic range and sensitivity of the assay were nevertheless superior to that observed using NFAT responsive effector cells and wild type Raji target cells (FIG. 3B).

Figure 4A:
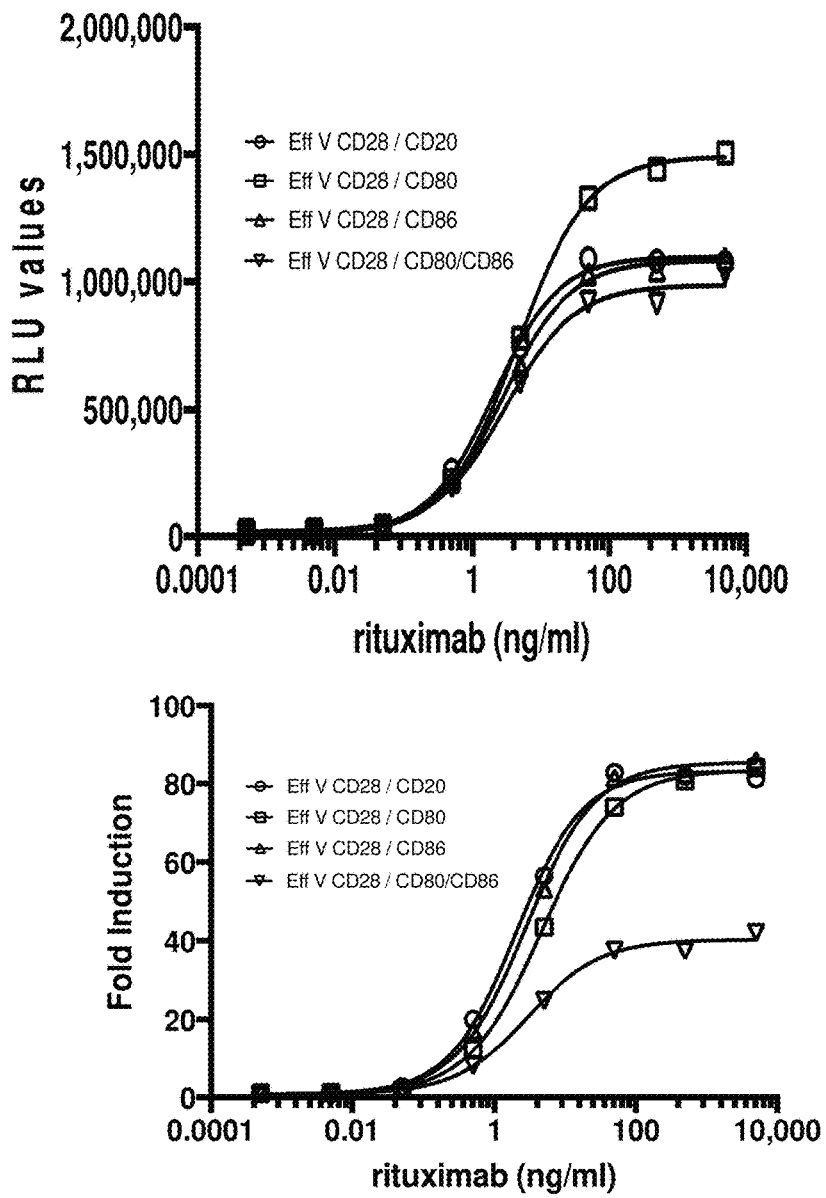
FIG. 4A illustrates the ADCC activity of rituximab using iLite® effector cells V-variant over-expressing CD28 and Raji target cells over-expressing both CD20 and the co-stimulatory molecules CD80, or CD86, or CD80 and CD86.

Over-expression of the co-stimulatory receptor CD28 in the recombinant Jurkat effector cells V-variant as described in Example 1 when used to assess the ADCC activity of rituximab in conjunction with Raji target cells over-expressing CD20 together with CD80, or CD86 or both CD80 and CD86 resulted in an ADCC assay with an increased FL signal (FIG. 4A, Table 1). The sensitivity of the ADCC assay was either marginally reduced or did not change significantly (FIG. 4A, Table 1), while the dynamic range of the ADCC assay was reduced when using target cells over-expressing CD80, or CD86 either alone or together with CD80 relative to target cells over-expressing CD20 alone, due to an overall increase in the FL signal in both the untreated control samples and the samples treated with rituximab (FIG. 4A, Table 1).

Figure 4B:
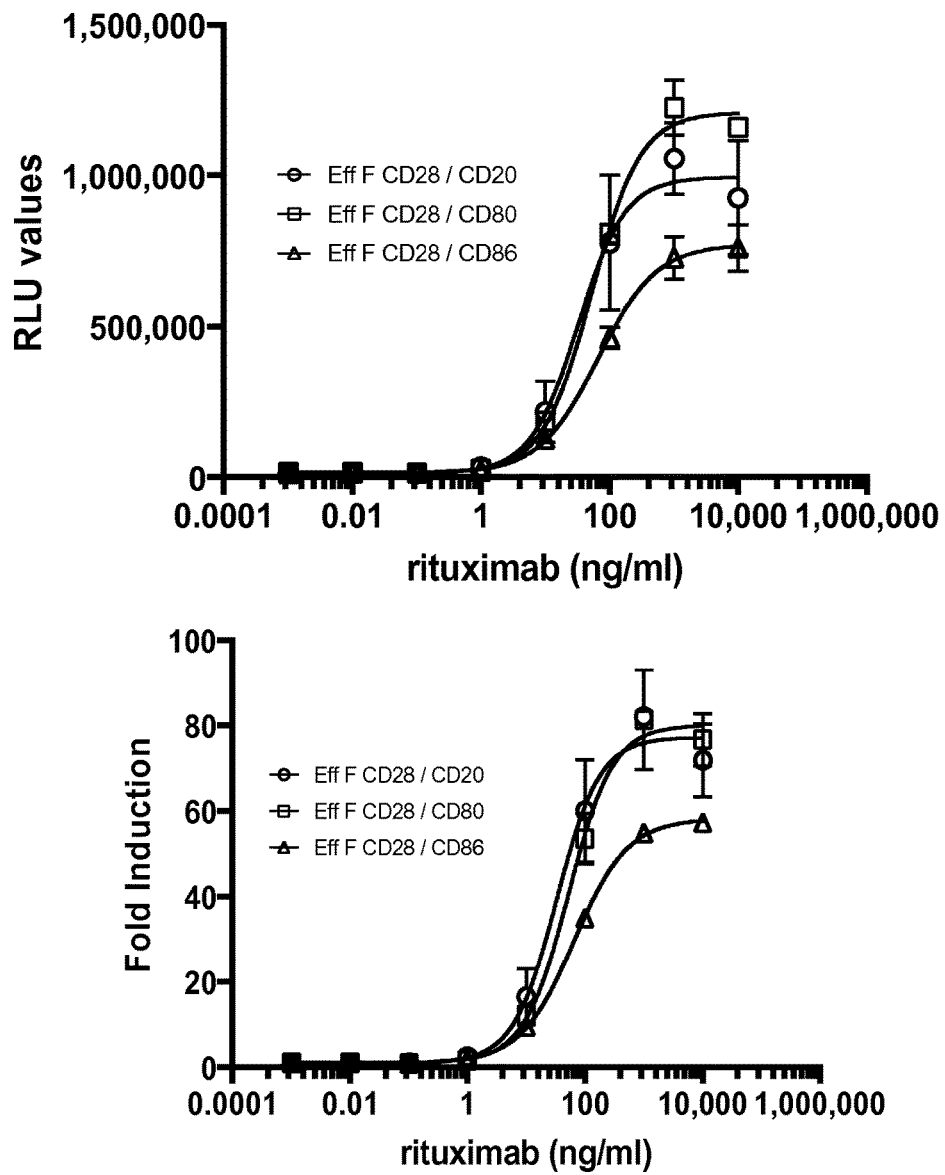
FIG. 4B illustrates the ADCC activity of rituximab using iLite® effector cells (F-variant) over-expressing CD28 and Raji target cells over-expressing both CD20 and the co-stimulatory molecules CD80, or CD86.

Over-expression of the co-stimulatory receptor CD28 in the recombinant Jurkat effector cells F-variant as described in Example 1 when used to assess the ADCC activity of rituximab in conjunction with Raji target cells over-expressing CD20 together with CD80, or CD86 resulted in an ADCC assay with an increased FL signal relative to the use of target cells overexpressing CD20 alone (FIG. 4B). The sensitivity of the ADCC assay was either unaffected or reduced slightly, however, relative to the use of target cells over-expressing CD20 alone (FIGS. 3B & 4B), while the dynamic range of the ADCC assay was reduced when using effector cells over-expressing CD28 and target cells over-expressing either CD80, or CD86 relative to target cells over-expressing CD20 alone, due to an overall increase in the FL signal in both the untreated control samples and the samples treated with rituximab (FIGS. 3B & 4B).

Over-expression of the co-stimulatory receptor CD28 in the recombinant Jurkat effector cells V-variant as described in Example 1 when used to assess the ADCC activity of rituximab in conjunction with Raji target cells over-expressing either CD20 alone or together with CD80, or CD86 or both CD80 and CD86 resulted in an ADCC assay with an enhanced dynamic range and markedly enhanced sensitivity relative to an ADCC assay using NFAT responsive effector cells and wild type Raji target cells (FIG. 3A). The maximal FL signal was, however, lower that that observed with NFAT responsive effector cells and wild type Raji target cells (FIG. 3A).

Figure 5A:
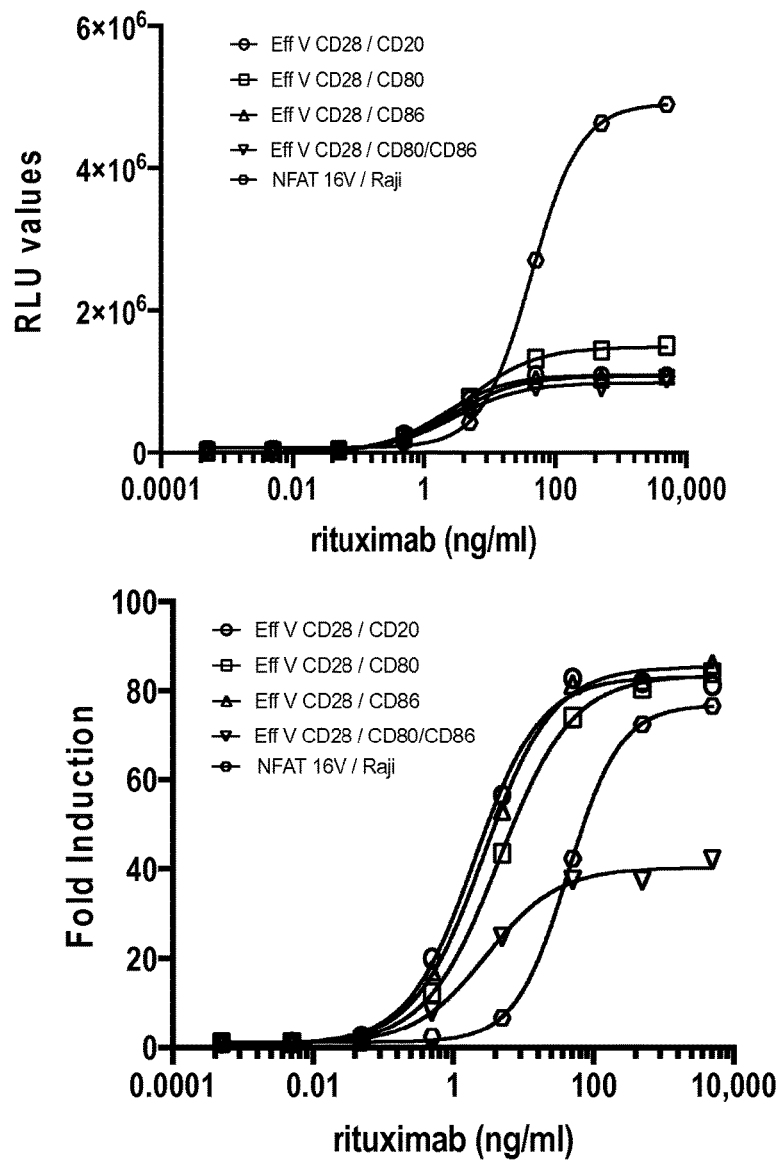
FIG. 5A illustrates a comparison of the ADCC activity of rituximab determined using the iLite® effector cells (V-variant) over-expressing CD28 and Raji target cells over-expressing both CD20 and the co-stimulatory molecules CD80, or CD86, or CD80 and CD86 versus NFAT responsive effector cells (V-variant) and wild type Raji target cells.
Figure 5B:
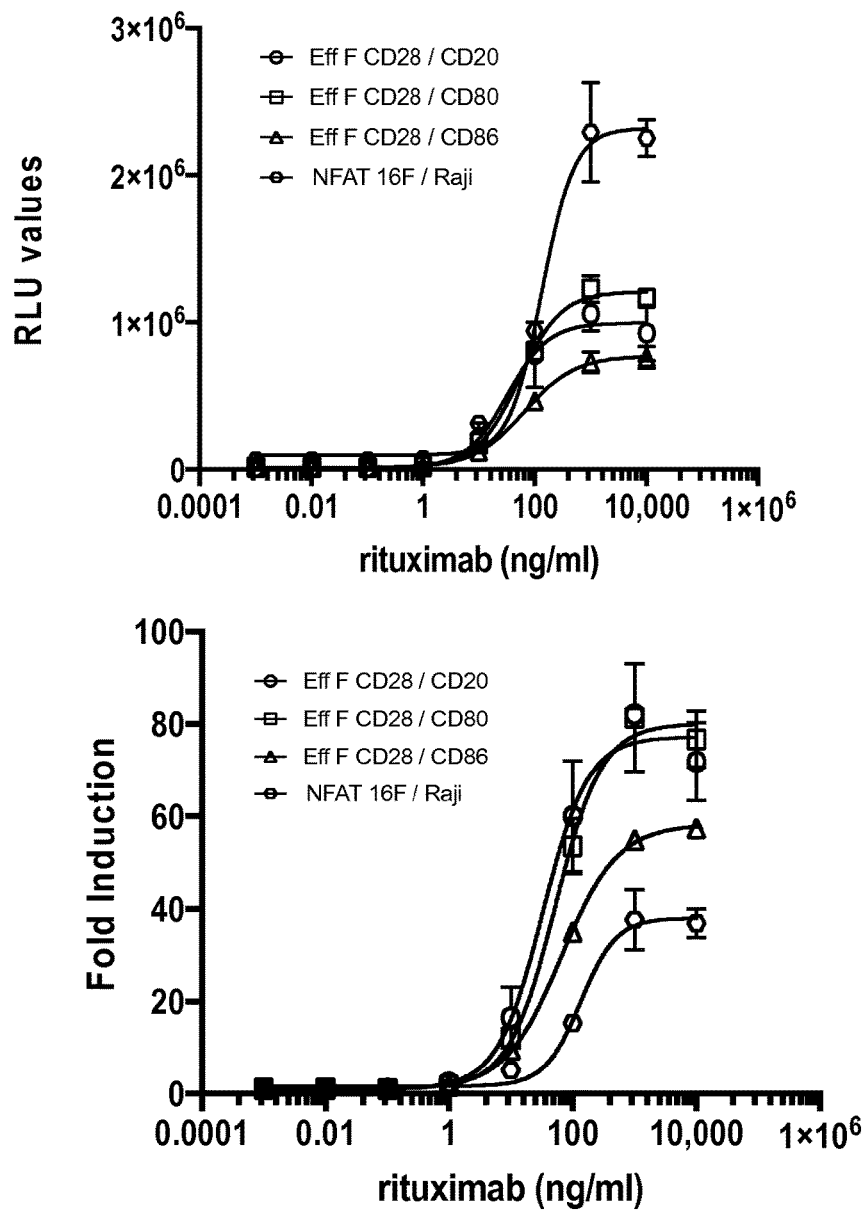
FIG. 5B illustrates a comparison of the ADCC activity of rituximab determined using the iLite® effector cells (F-variant) over-expressing CD28 and Raji target cells over-expressing both CD20 and the co-stimulatory molecules CD80, or CD86 versus NFAT responsive effector cells (F-variant) and wild type Raji target cells.

The use of the Jurkat effector cells expressing the F-variant of CD16A and overexpressing CD28 as described in Example 1 together with Raji target cells overexpressing CD20 together with CD80, or CD86, or CD80 and CD86 to assess the ADCC activity of rituximab resulted in an ADCC assay with an increased dynamic range and sensitivity relative to an ADCC assay using NFAT responsive effector cells expressing the F-variant of CD16A and wild type Raji target cells (FIG. 3B). In contrast, the maximal FL signal of the assay was greater when using NFAT responsive effector cells expressing the F-variant of CD16A and wild type Raji target cells (FIG. 5B).

The effector cells expressing the H-131 variant of CD32A described in Example 4 expressed an enhanced FL signal, dynamic range and sensitivity when used to assess the ADCP activity of rituximab in conjunction with recombinant Raji target cells over-expressing CD20 together with CD80, or CD86, or both CD80 and CD86 relative to an ADCP assay using said effector cells and target cells over-expressing CD20 alone.

The effector cells expressing the H-131 variant of CD32A described in Example 4 expressed an enhanced FL signal, dynamic range and sensitivity when used to assess the ADCP activity of rituximab in conjunction with recombinant Raji target cells over-expressing CD20 together with CD80, or CD86 or both CD80 and CD86 relative to an ADCP assay using effector cells expressing FcγRI IA functionally linked to the FL reporter-gene under the control of a NFAT chimeric promoter and wild type Raji target cells.

Example 6: Establishment of an Engineered Target Cell Line Expressing High Constant Levels of erbB2 and One or More Co-Stimulatory Molecules at the Cell Surface HEK293 cells (ATCC® CRL 1573) over-expressing a constant high level of erbB2 previously disclosed in WO 2018/065401 were transfected with the co-stimulatory molecule CD80 or CD86 or both CD80 and CD86 using the FuGENE HD transfection reagent (Promega Catalogue N° E2311). Positive clones were enriched using fluorescent activated cell sorting and phycerythrin labelled anti-CD80 (ImmunoTools, Catalogue N° 21270804) or FITC labelled anti-CD86 (ImmunoTools, Catalogue N° 21480863) monoclonal antibodies. Stable clones were isolated and characterized for ADCC activity in the presence of the ADCC effector cells previously disclosed in WO 2018/065401 and trastuzumab and then sub-cloned. Suitable sub-clones were isolated, characterized and propagated giving rise to erbB2++ target cell lines over-expressing CD80, or CD86, or both CD80 and CD86.

Vials of iLite® effector cells disclosed in WO 2018/065401 and vials of erbB2++ target cells over-expressing CD80, or CD86, or both CD80 and CD86 were frozen separately using standard techniques. Upon thawing, effector cells and target cells were mixed at E:T ratio of 4:1 and incubated for 6 hours in a 96-well white-sided microtiter plate (Perkin Elmer 6005181) in the presence of increasing concentrations of trastuzumab in RPMI 1640 culture medium+10% fetal bovine serum (FBS). FL activity was then determined using the Dual Glo (Promega 22920) dual luciferase substrate and light emission was quantified in a luminometer (GloMax, Promega) and expressed as relative luciferase units (RLU). Results are presented in the form of a 4-parametric logistic (4PL) plot as shown in FIGS. 6 to 9. The associated Table to the Figures and Table 2 outline the principal parameters of a 4PL plot for the iLite® effector cells and erbB2++ target cells.

Figure 6A:
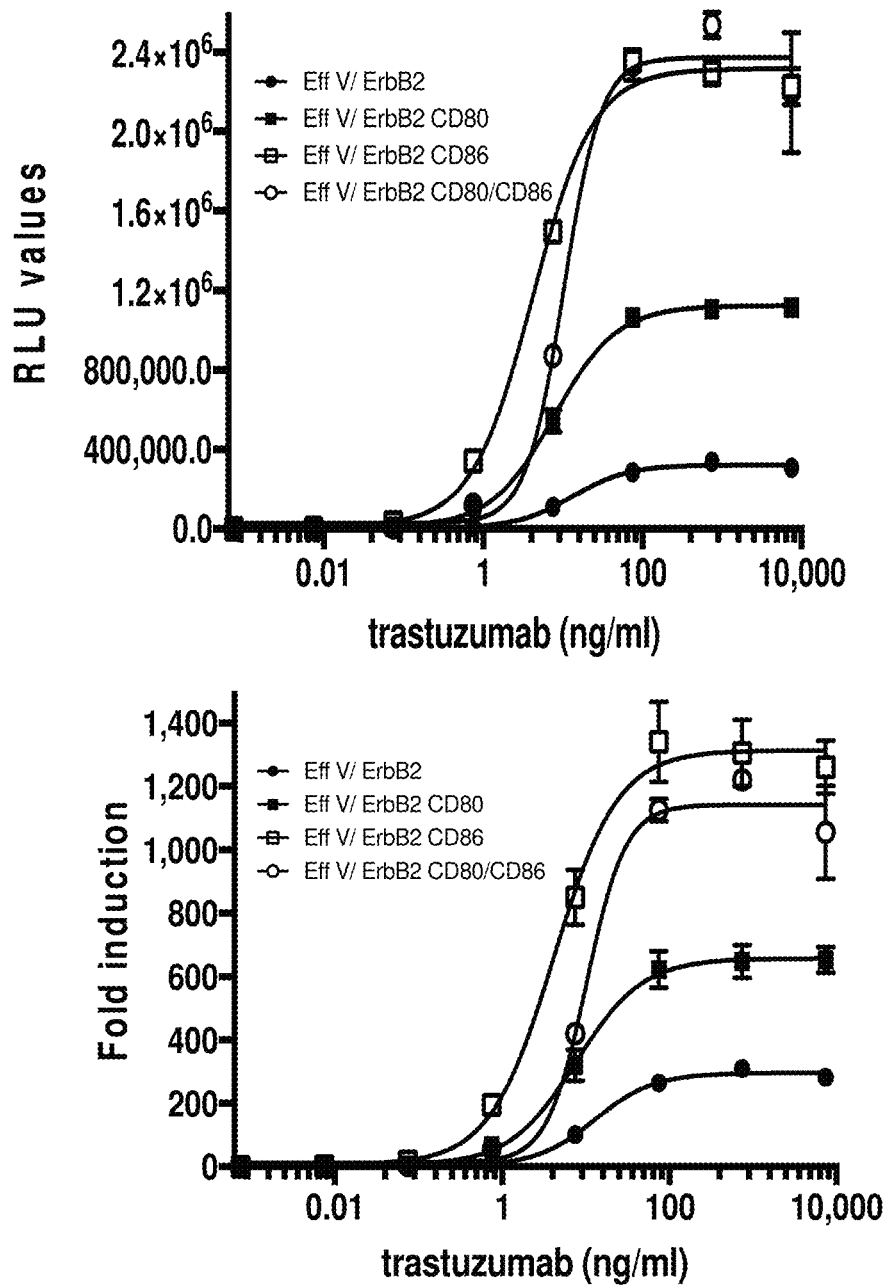
FIG. 6A illustrates a comparison of the ADCC activity of trastuzumab determined using the iLite® effector cells (V-variant) and HEK293 target cells over-expressing either erbB2 alone or over-expressing both erbB2 and the co-stimulatory molecules CD80, or CD86, or CD80 and CD86.

When said cells overexpressing erbB2 were used to assess the ADCC activity of trastuzumab in conjunction with the ADCC V-variant effector cells previously disclosed in WO 2018/065401 the increase in the maximal FL signal and dynamic range of the ADCC assay were most pronounced using target cells over-expressing both erbB2 and CD86 (FIG. 6A). An increased FL signal and dynamic range were also observed using target cells over-expressing erbB2 and CD80 or erbB2 and CD80 & CD86 relative to cells over-expressing erbB2 alone (Figure A, Table 1). Over expression of the co-stimulatory molecules CD80, or CD86, or CD80 and CD86 also increased the sensitivity of the assay. The greatest increase in sensitivity was observed using target cells over-expressing erbB2 and CD86 followed by target cells expressing erbB2 and CD80 while only a modest increase in sensitivity was observed using target cells over-expressing erbB2 and both CD80 and CD86 (FIG. 6A, Table 2).

Figure 6B:
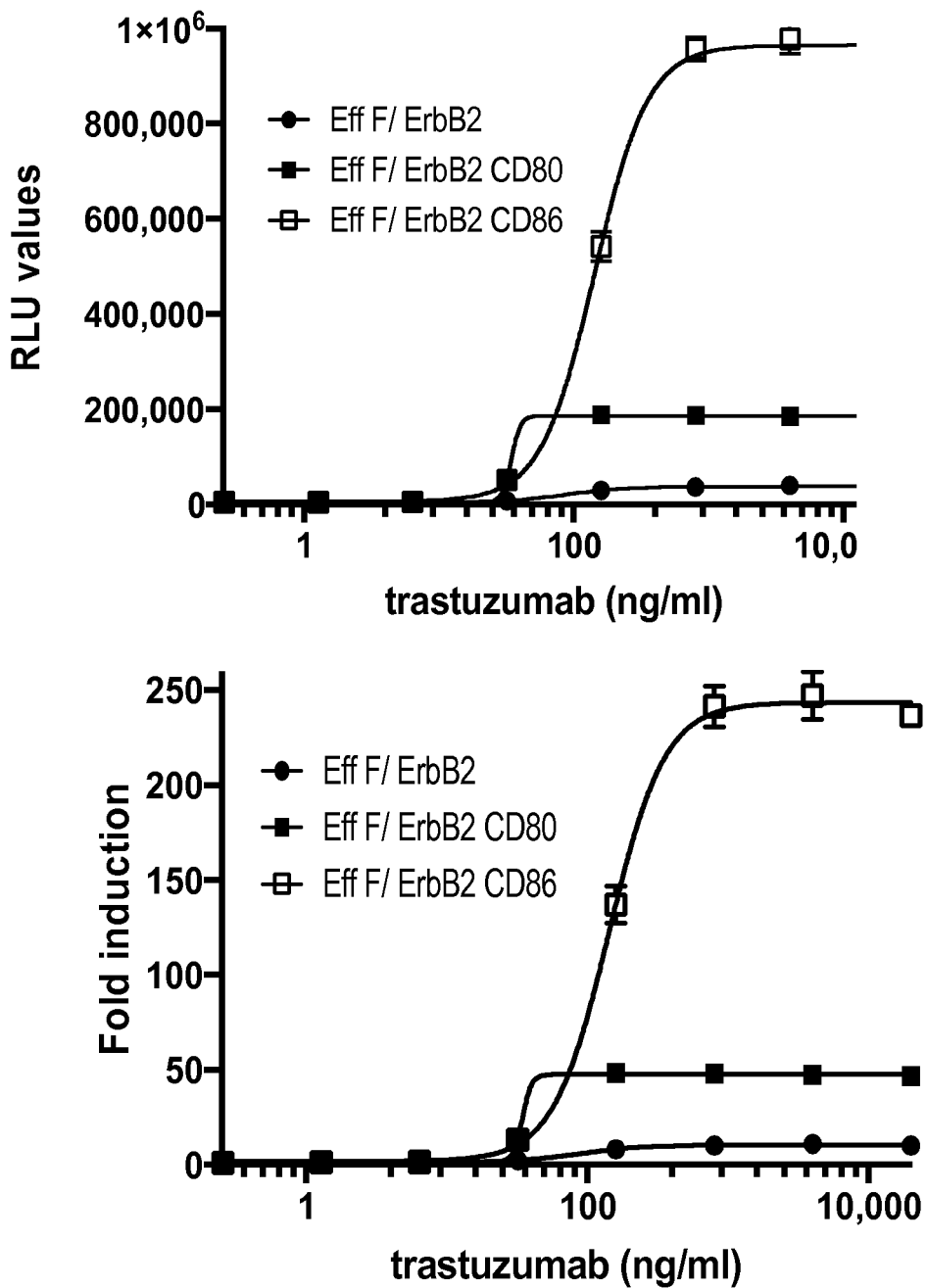
FIG. 6B illustrates a comparison of the ADCC activity of trastuzumab determined using the iLite® effector cells (F-variant) and HEK293 target cells over-expressing either erbB2 alone or over-expressing both erbB2 and the co-stimulatory molecules CD80, or CD86.

Jurkat effector cells expressing the F-variant of CD16A as disclosed in WO 2018/065401 when used to assess the ADCC activity of trastuzumab in conjunction with HEK293 target cells over-expressing both erbB2 and CD80, or erbB2 and CD86 resulted in an ADCC assay with a markedly increased FL signal and dynamic range (FIG. 6B). The sensitivity of the ADCC assay was also increased using target cells overexpressing both erbB2 and CD80 but was decreased when using target cells over-expressing erbB2 and CD86 (FIG. 6B).

Figure 7A:
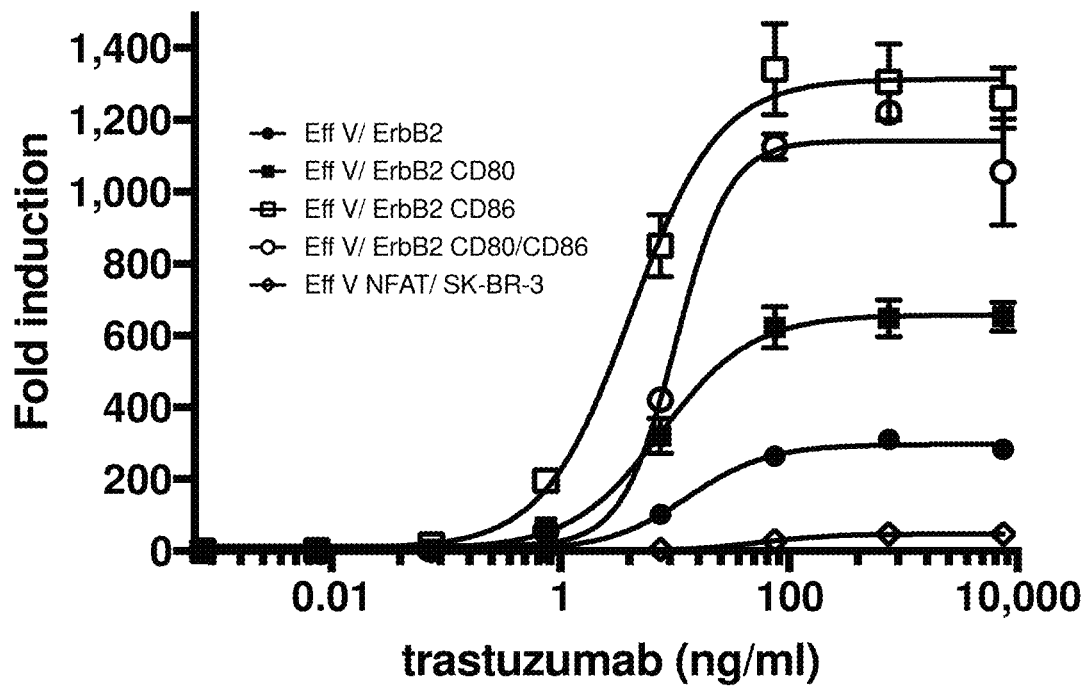
FIG. 7A illustrates a comparison of the ADCC activity of trastuzumab determined using the iLite® effector cells (V-variant) and HEK293 target cells over-expressing both erbB2 and the co-stimulatory molecules CD80, or CD86, or CD80 and CD86 versus NFAT responsive effector cells (V-variant) and wild type SK-BR-3 target cells.

Said HEK293 target cells over-expressing erbB2 alone or together with CD80, or CD86 or both CD80 and CD86 together when used to assess the ADCC activity of trastuzumab in conjunction with the ADCC V-variant effector cells previously disclosed in WO 2018/065401 resulted in an ADCC assay with a markedly enhanced dynamic range and sensitivity relative to an ADCC assay using NFAT responsive effector cells and wild type SK-BR-3 target cells (FIG. 7A). The maximal FL signal was also increased relative to that observed with NFAT responsive effector cells and wild type Raji target cells when target cells over-expressing erbB2 and CD86, or both CD80 and CD86 were to assess the ADCC activity of trastuzumab in conjunction with the ADCC V-variant effector cells previously disclosed in WO 2018/065401 (FIG. 7A).

Figure 7B:
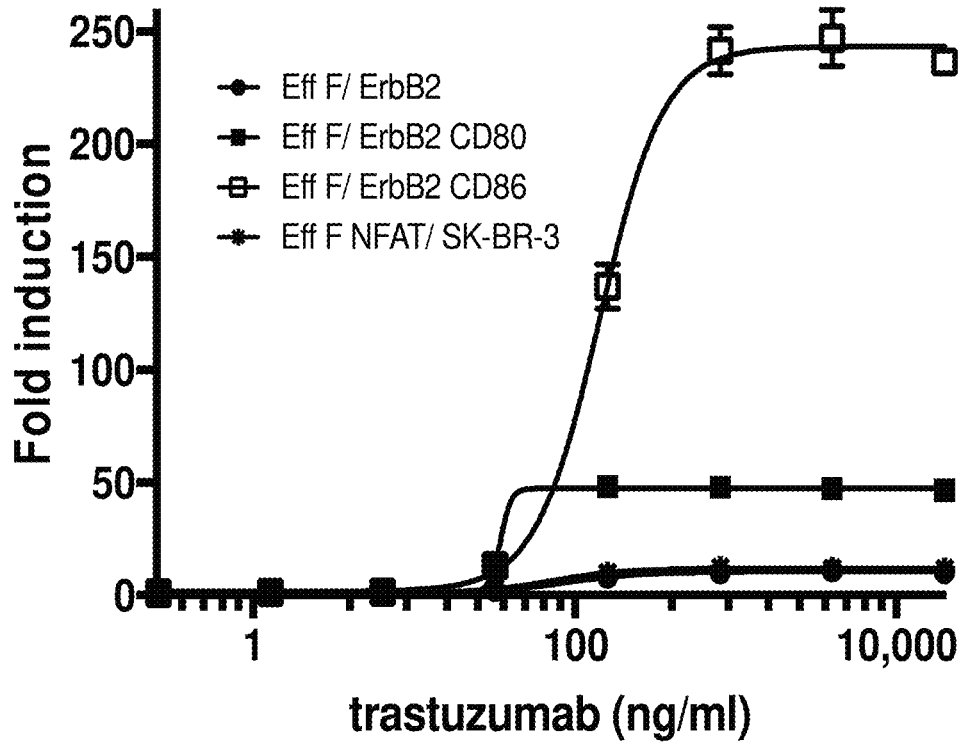
FIG. 7B illustrates a comparison of the ADCC activity of trastuzumab determined using the iLite® effector cells (F-variant) and HEK293 target cells over-expressing both erbB2 and the co-stimulatory molecules CD80, or CD86 versus NFAT responsive effector cells (F-variant) and wild type SK-BR-3 target cells.

The use of HEK293 target cells over-expressing erbB2 alone or together with CD80, or CD86 to assess the ADCC activity of trastuzumab in conjunction with the ADCC F-variant effector cells previously disclosed in WO 2018/065401 resulted in an ADCC assay with a markedly enhanced FL signal and dynamic range relative to an ADCC assay using NFAT responsive effector cells expressing the F-variant of CD16A and wild type SK-BR-3 target cells (FIG. 7B). The sensitivity of the ADCC assay was also increased using target cells overexpressing both erbB2 and CD80 but not when using target cells expressing both erbB2 and CD86 (FIG. 7B).

Figure 8A:
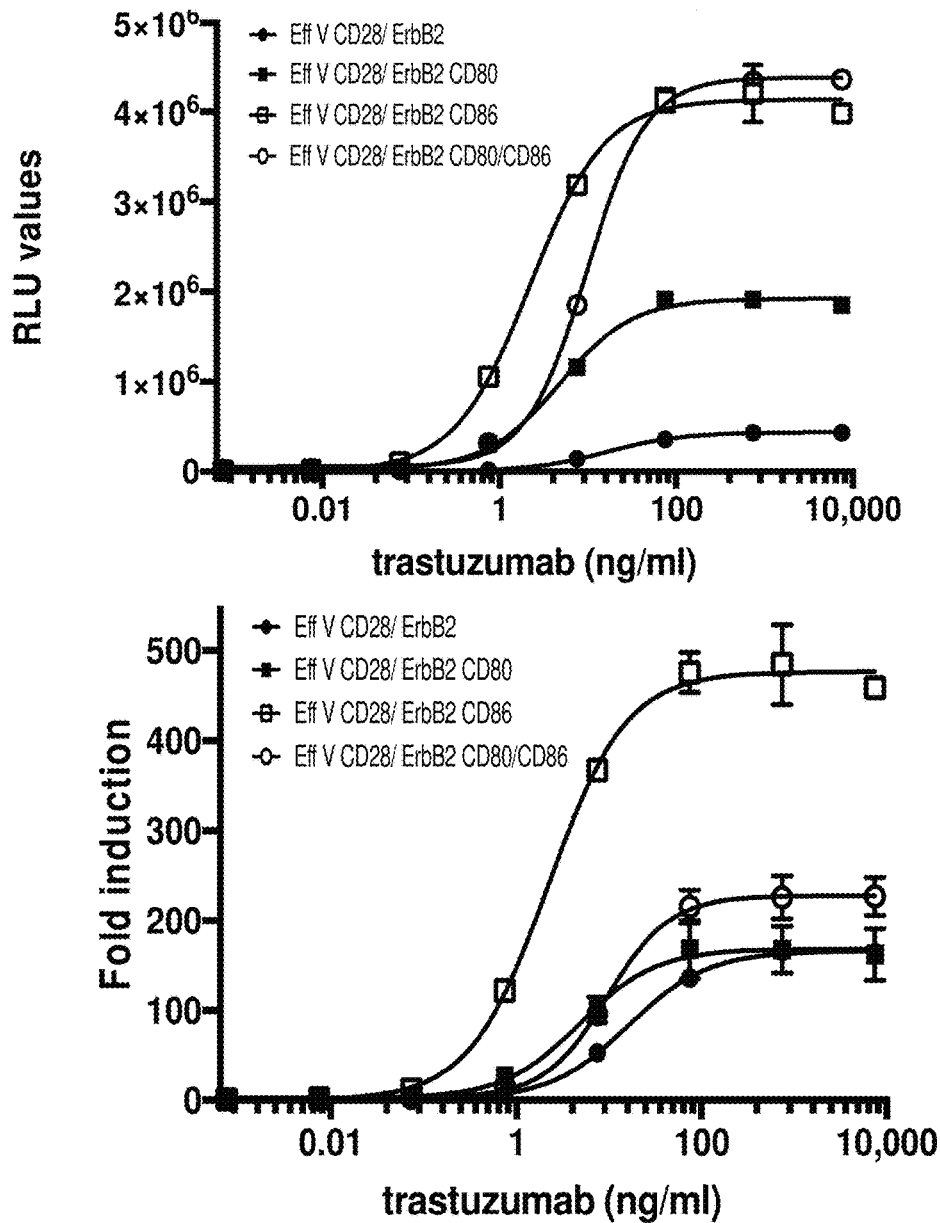
FIG. 8A illustrates the ADCC activity of trastuzumab using iLite® effector cells (V-variant) over-expressing CD28 and HEK293 target cells over-expressing both erbB2 and the co-stimulatory molecules CD80, or CD86, or CD80 and CD86.

Over-expression of the co-stimulatory receptor CD28 in the recombinant Jurkat effector cells V-variant as described in Example 1 when used to assess the ADCC activity of trastuzumab in conjunction with HEK293 target cells over-expressing erbB2 together with CD80, or CD86, or CD80 together with CD86 resulted in an ADCC assay with an increased FL signal, dynamic range and sensitivity relative to the use of Jurkat effector cells overexpressing CD28 and target cells overexpressing erbB2 alone (FIG. 8A, Table 2).

Figure 8B:
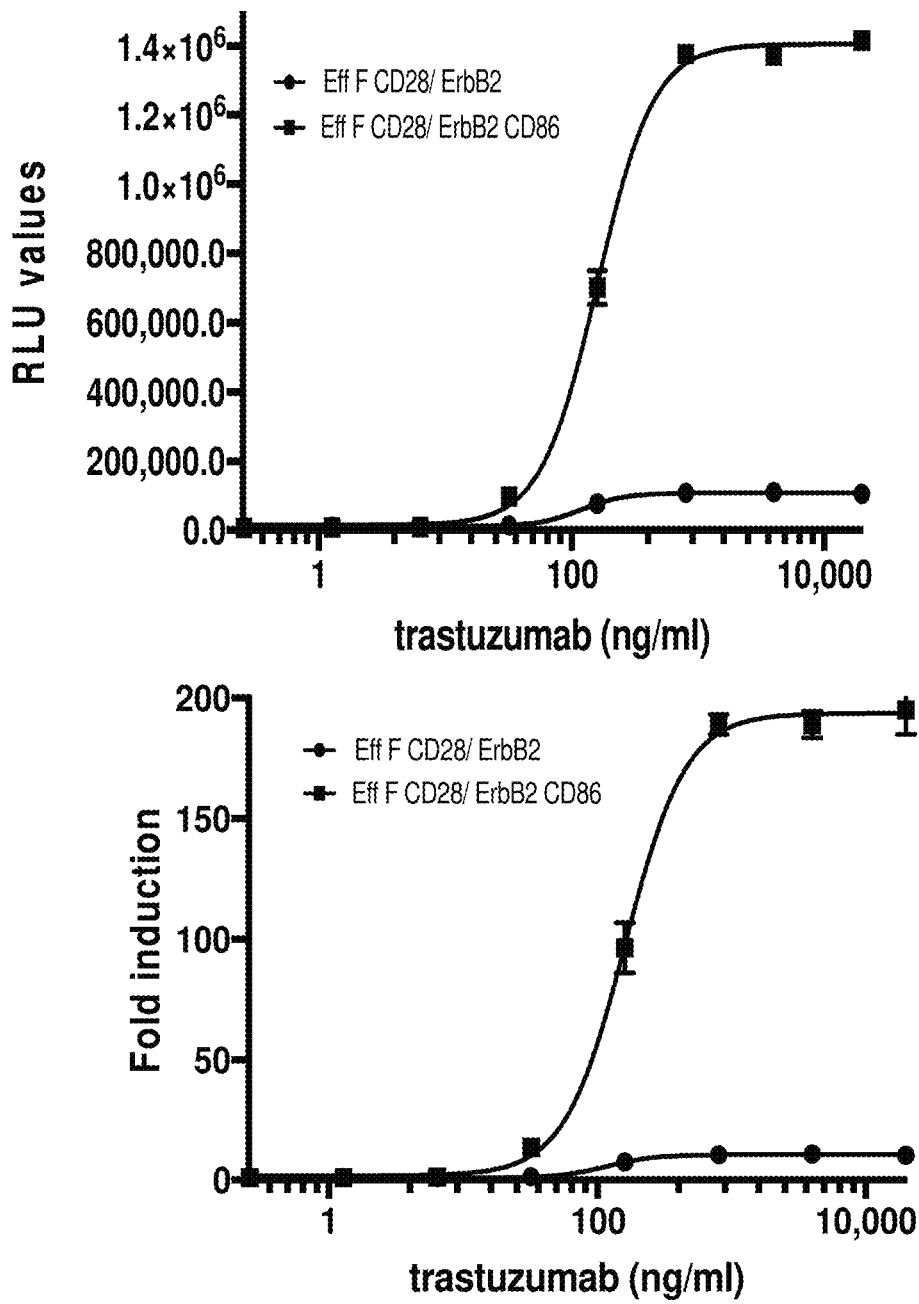
FIG. 8B illustrates the ADCC activity of trastuzumab using iLite® effector cells (F-variant) over-expressing CD28 and HEK293 target cells over-expressing both erbB2 and the co-stimulatory molecule CD86.

Over-expression of the co-stimulatory receptor CD28 in the recombinant Jurkat effector cells F-variant as described in Example 1 when used to assess the ADCC activity of trastuzumab in conjunction with HEK293 target cells over-expressing erbB2 together with CD86 resulted in an ADCC assay with an increased FL signal and dynamic range but reduced sensitivity (FIG. 8B).

Figure 9A:
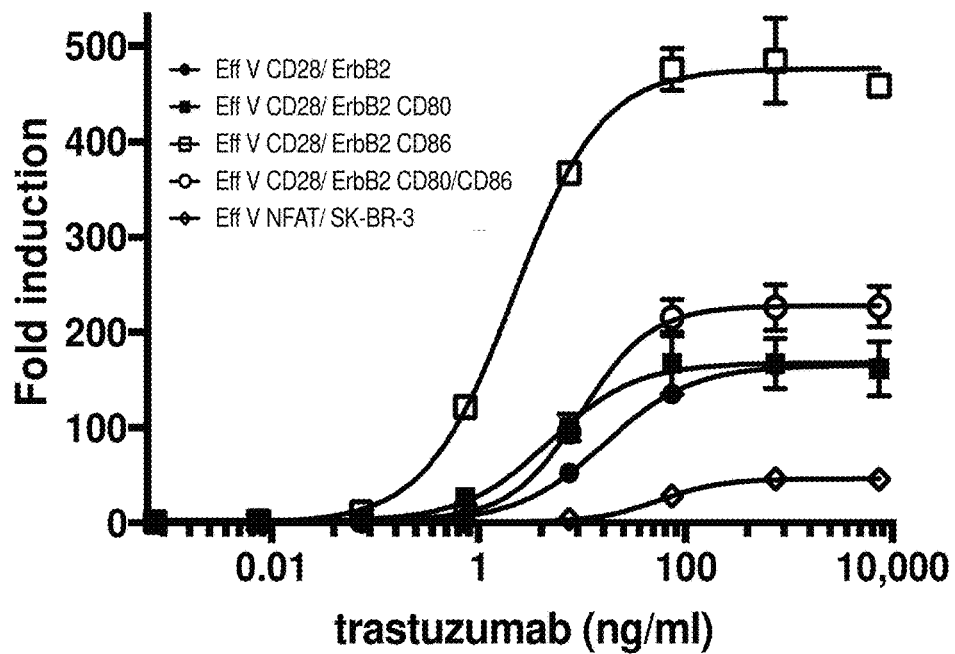
FIG. 9A illustrates a comparison of the ADCC activity of trastuzumab determined using the iLite® effector cells (V-variant) over-expressing CD28 and HERK293 target cells over-expressing both erbB2 and the co-stimulatory molecules CD80, or CD86, or CD80 and CD86 versus NFAT responsive effector cells (V-variant) and wild type SK-BR-3 target cells.

Over-expression of the co-stimulatory receptor CD28 in the recombinant Jurkat effector cells V-variant as described in Example 1 when used to assess the ADCC activity of trastuzumab in conjunction with HEK293 target cells over-expressing erbB2 together with CD86 resulted in an ADCC assay with an increased FL signal, dynamic range and sensitivity relative to an ADCC using NFAT responsive effector cells expressing the V-variant of CD16A and wild type SK-BR-3 target cells as shown in FIG. 9A.

Figure 9B:
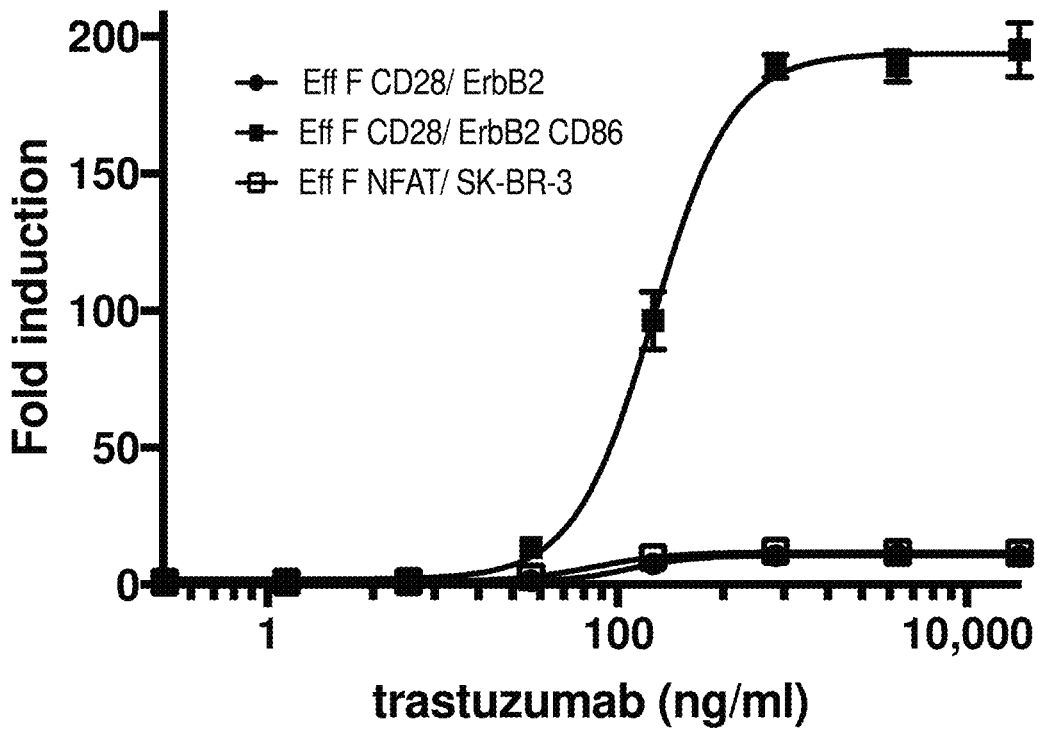
FIG. 9B illustrates a comparison of the ADCC activity of trastuzumab determined using the iLite® effector cells (F-variant) over-expressing CD28 and HERK293 target cells over-expressing both erbB2 and the co-stimulatory molecule CD86 versus NFAT responsive effector cells (F-variant) and wild type SK-BR-3 target cells.

Over-expression of the co-stimulatory receptor CD28 in the recombinant Jurkat effector cells F-variant as described in Example 1 when used to assess the ADCC activity of trastuzumab in conjunction with HEK293 target cells over-expressing erbB2 together with CD86 resulted in an ADCC assay with an increased FL signal and dynamic range but reduced sensitivity relative to an ADCC using NFAT responsive effector cells expressing the F-variant of CD16A and wild type SK-BR-3 target cells (FIG. 9B).

The effector cells expressing the H-131 variant of CD32A described in Example 4 expressed an enhanced FL signal, dynamic range and sensitivity when used to assess the ADCP activity of trastuzumab in conjunction with recombinant HEK293 target cells over-expressing erbB2 together with CD80, or CD86, or both CD80 and CD86 relative to an ADCP assay using said effector cells and target cells over-expressing erbB2 alone.

The effector cells expressing the H-131 variant of CD32A described in Example 4 expressed an enhanced FL signal, dynamic range and sensitivity when used to assess the ADCP activity of trastuzumab in conjunction with recombinant HEK293 target cells over-expressing erbB2 together with CD80, or CD86, or both CD80 and CD86 relative to an ADCP assay using effector cells expressing FcγRIIA functionally linked to the FL reporter-gene under the control of a NFAT chimeric promoter and wild type SK-BR-3 target cells.

Example 7: Establishment of an Engineered Target Cell Line Expressing High Constant Levels of EGFR and One or More Co-Stimulatory Molecules at the Cell Surface HEK293 cells (ATCC® CRL 1573) over-expressing a constant high level of EGFR previously disclosed in WO 2018/065401 were transfected with the co-stimulatory molecule CD80, or CD86, or both CD80 and CD86 using the FuGENE HD transfection reagent (Promega Catalogue N° E2311). Positive clones were enriched using fluorescent activated cell sorting and phycerythrin labelled anti-CD80 (ImmunoTools, Catalogue N° 21270804) or FITC labelled anti-CD86 (ImmunoTools, Catalogue N° 21480863) monoclonal antibodies. Stable clones were isolated and characterized for ADCC activity in the presence of the ADCC effector cells previously disclosed in WO 2018/065401 and cetuximab and then sub-cloned. Suitable sub-clones were isolated, characterized and propagated giving rise to EGFR$^{++}$ target cell lines over-expressing CD80, or CD86, or both CD80 and CD86. Vials of iLite® effector cells disclosed in WO 2018/065401 and vials of EGFR$^{++}$ target cells over-expressing CD80, or CD86, or both CD80 and CD86 were frozen separately using standard techniques. Upon thawing, effector cells and target cells were mixed at E:T ratio of 4:1 and incubated for 6 hours in a 96-well white-sided microtiter plate (Perkin Elmer 6005181) in the presence of increasing concentrations of cetuximab in RPMI 1640 culture medium+10% fetal bovine serum (FBS). FL activity was then determined using the Dual Glo (Promega 22920) dual luciferase substrates and light emission was quantified in a luminometer (GloMax, Promega) and expressed as relative luciferase units (RLU). Results are presented in the form of a 4-parametric logistic (4PL) plot as shown in FIGS. 10 to 13. The associated Table to the Figures and Table 3 outline the principal parameters of a 4PL plot for the iLite® effector cells and EGFR$^{++}$ target cells.

Figure 10A:
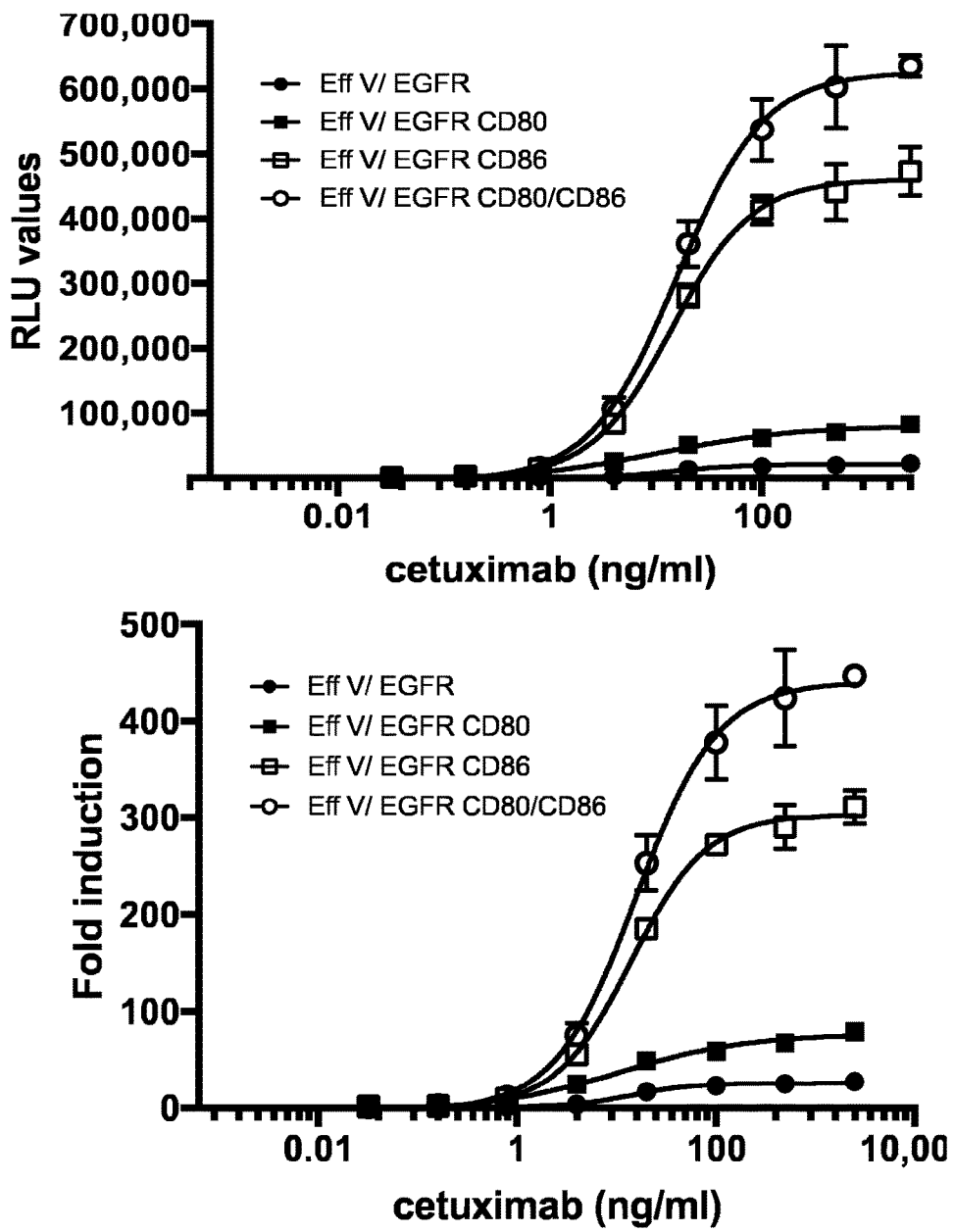
FIG. 10A illustrates a comparison of the ADCC activity of cetuximab determined using the iLite® effector cells (V-variant) and HEK293 target cells over-expressing either EGFR alone or both EGFR and the co-stimulatory molecules CD80, or CD86, or CD80 and CD86.

When said target cells were used to assess the ADCC activity of cetuximab in conjunction with the ADCC V-variant effector cells previously disclosed in WO 2018/065401 the maximal FL signal and dynamic range of the ADCC assay were most pronounced using target cells over-expressing both CD80 and CD86. An increased FL signal and dynamic range were also observed using target cells over-expressing CD80 or CD86 relative to cells over-expressing EGFR alone (FIG. 10A, Table 3). Over expression of the co-stimulatory molecules CD80 or CD86 also increased the sensitivity of the assay while over-expression of both CD80 and CD86 together decreased the sensitivity of the assay (FIG. 10A, Table 3).

Figure 10B:
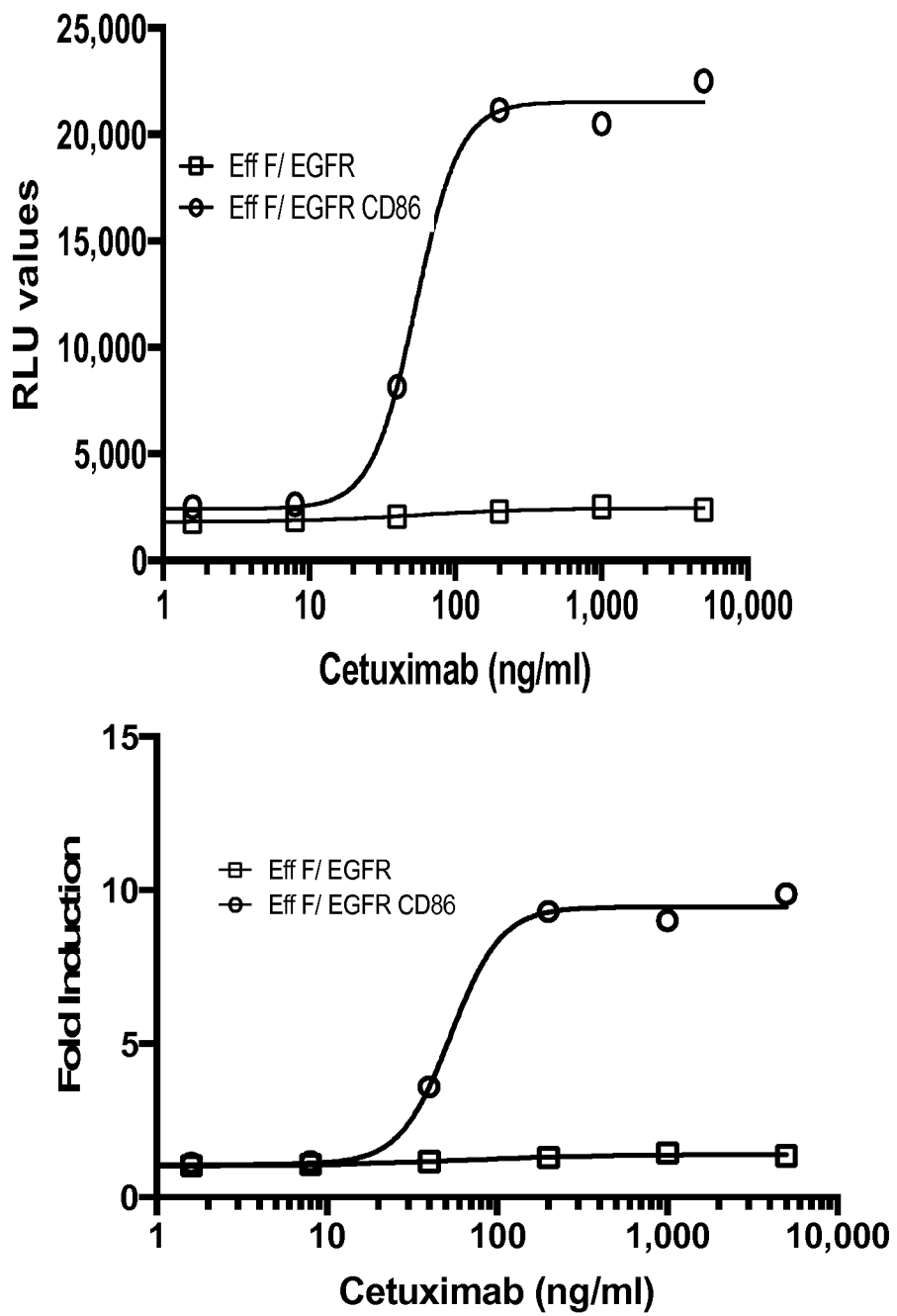
FIG. 10B illustrates a comparison of the ADCC activity of cetuximab determined using the iLite® effector cells (F-variant) and HEK293 target cells over-expressing either EGFR alone or both EGFR and the co-stimulatory molecule CD86.

The use of target cells overexpressing both EGFR and CD86 to assess the ADCC activity of cetuximab in conjunction with the ADCC effector cells expressing the F-variant of CD16A previously disclosed in WO 2018/065401 resulted in an ADCC assay with an increased FL signal and dynamic range relative to the use of target cells overexpressing EGFR alone although the sensitivity of the assay did not change significantly (FIG. 10B).

The use of HEK293 target cells over-expressing EGFR together with CD80, CD86 or both CD80 and CD86 together to assess the ADCC activity of cetuximab in conjunction with the ADCC V-variant effector cells previously disclosed in WO 2018/065401, resulted in an ADCC assay with a markedly enhanced dynamic range and enhanced sensitivity relative to an ADCC assay using NFAT responsive effector cells and wild type A431 target cells. In contrast, the maximal FL signal observed with NFAT responsive effector cells and wild type A431 target cells was greater than that observed with the ADCC V-variant effector cells previously disclosed in WO 2018/065401 and target cells over-expressing EGFR and one or more co-stimulatory molecules (FIG. 11A, Table 3).

The use of HEK293 target cells over-expressing EGFR together with CD86 to assess the ADCC activity of cetuximab in conjunction with the ADCC effector cells expressing the F-variant of CD16A previously disclosed in WO 2018/065401, resulted in an ADCC assay with an enhanced sensitivity but unchanged dynamic range relative to an ADCC assay using NFAT responsive effector cells and wild type A431 target cells. In contrast, the maximal FL signal observed with NFAT responsive effector cells and wild type A431 target cells was greater than that observed with the ADCC V-variant effector cells previously disclosed in WO 2018/065401 and target cells over-expressing EGFR and one or more co-stimulatory molecules (FIG. 11B).

Figure 11A:
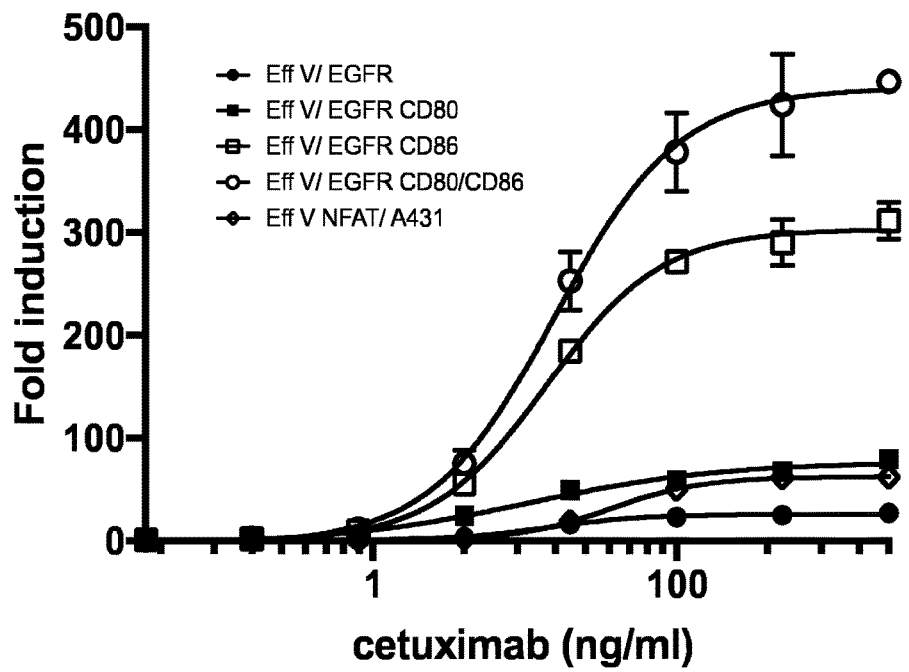
FIG. 11A illustrates a comparison of the ADCC activity of cetuximab determined using the iLite® effector cells (V-variant) and HEK293 target cells over-expressing both EGFR and the co-stimulatory molecules CD80, or CD86, or CD80 and CD86 versus NFAT responsive effector cells (V-variant) and wild type A431 target cells.
Figure 11B:
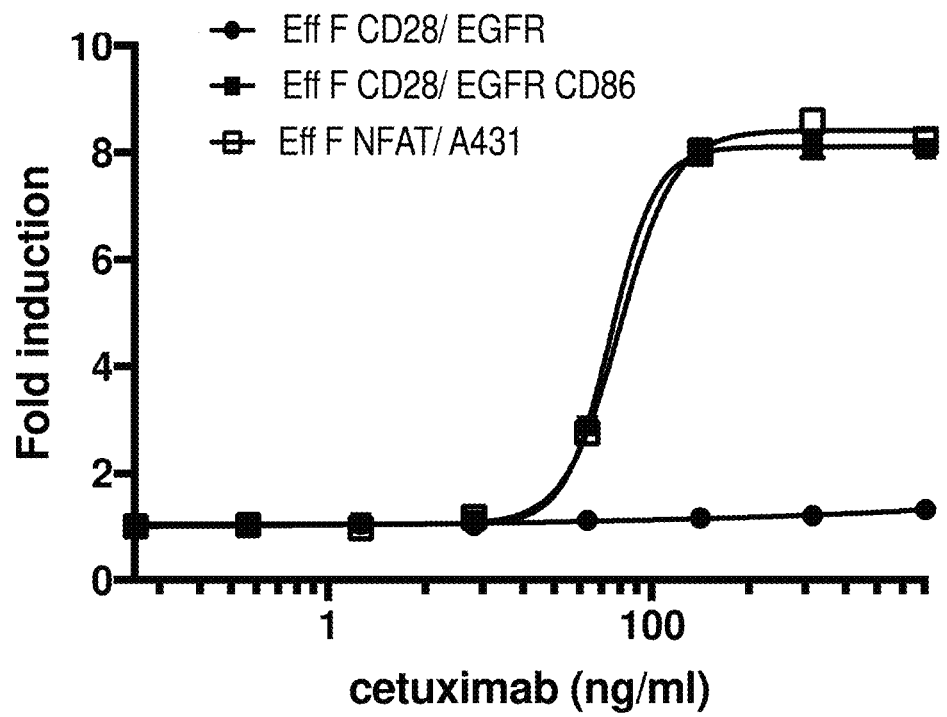
FIG. 11B illustrates a comparison of the ADCC activity of cetuximab determined using the iLite® effector cells (F-variant) and HEK293 target cells over-expressing both EGFR and the co-stimulatory molecule CD86 versus NFAT responsive effector cells (F-variant) and wild type A431 target cells.
Figure 12A:
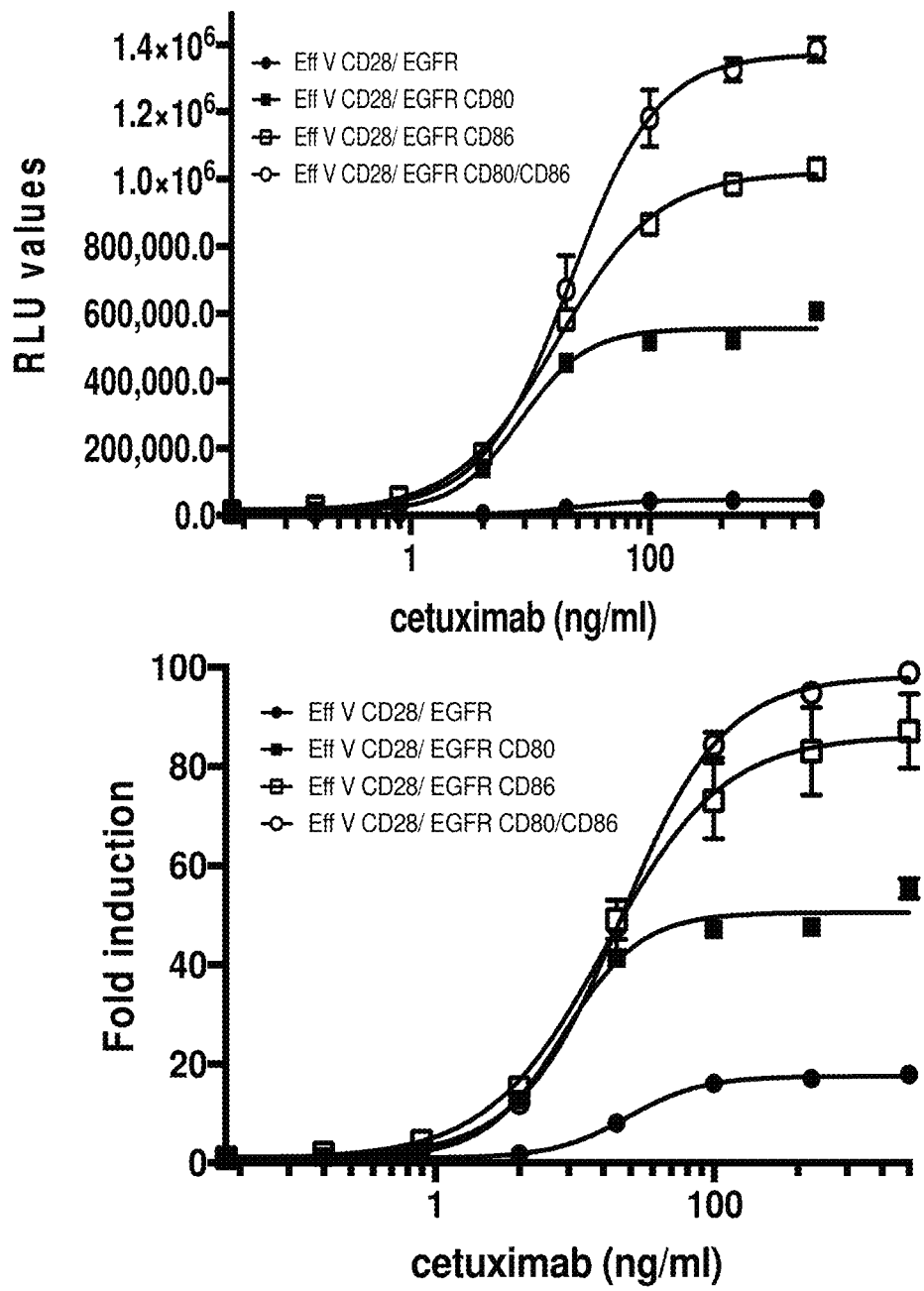
FIG. 12A illustrates the ADCC activity of cetuximab using iLite® effector cells (V-variant) over-expressing CD28 and HEK293 target cells over-expressing both EGFR and the co-stimulatory molecules CD80, or CD86 or CD80 and CD86.

The use of recombinant Jurkat effector cells expressing the V-variant of CD16A and over-expressing the co-stimulatory receptor CD28 as described in Example 1 to assess the ADCC activity of cetuximab in conjunction with HEK293 target cells over-expressing EGFR together with CD80, or CD86 or both CD80 and CD86 resulted in an ADCC assay with a markedly increased FL signal and dynamic range relative to an ADCC assay using Jurkat effector cells expressing endogenous levels of CD28 as disclosed in WO 2018/065401 and target cells overexpressing EGFR alone (FIGS. 11A & 12A, Table 3). The sensitivity of the ADCC assay was also increased relative to the use of effector cells expressing endogenous levels of CD28 when using target cells over-expressing CD80, or CD86 but only marginally when using target cells overexpressing both EGFR and CD80 together with CD86 (FIG. 12A, Table 3).

Figure 12B:
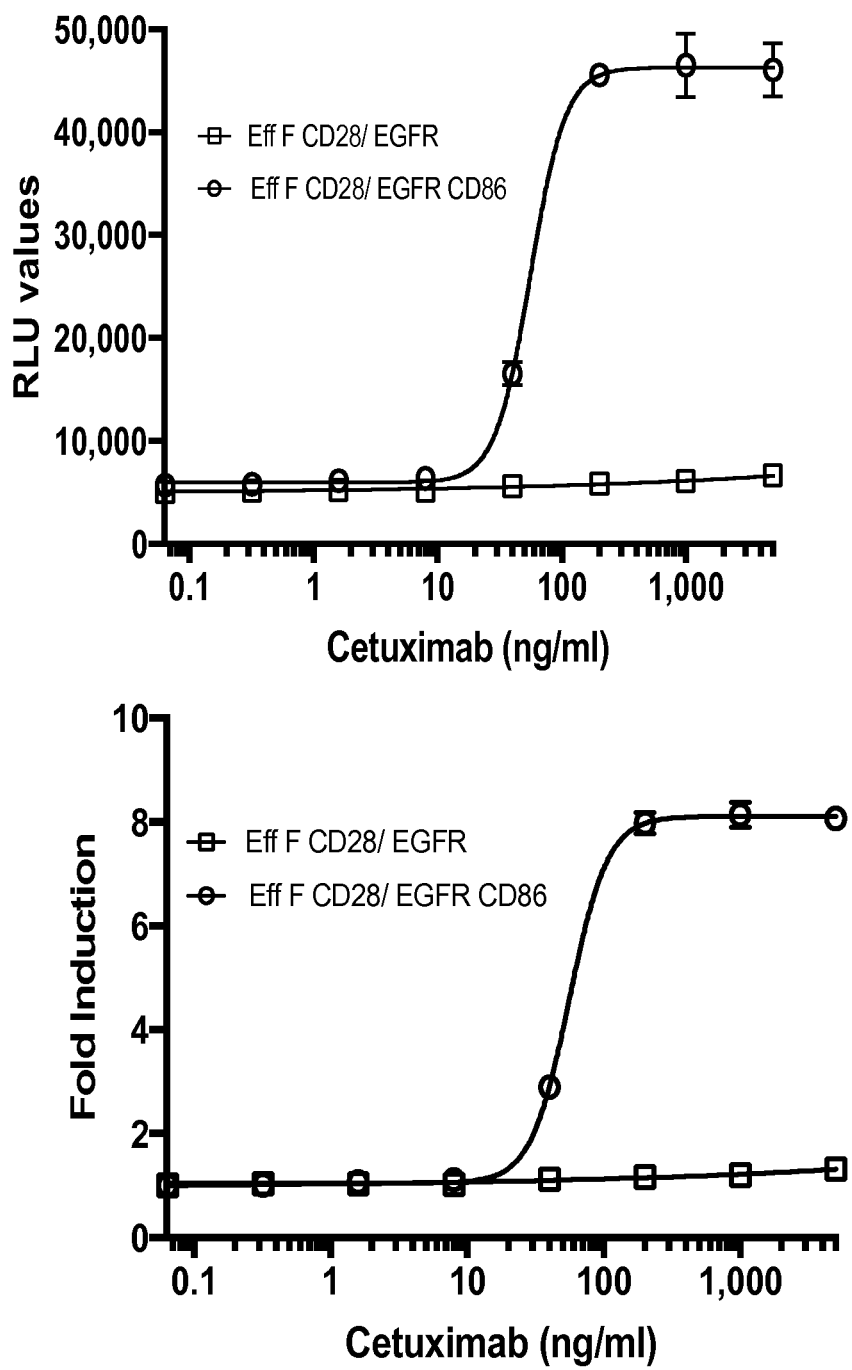
FIG. 12B illustrates the ADCC activity of cetuximab using iLite® effector cells (F-variant) over-expressing CD28 and HEK293 target cells over-expressing both EGFR and the co-stimulatory molecule CD86.

The use of Jurkat effector cells expressing the F-variant of CD16A and overexpressing the co-stimulatory receptor CD28 as described in Example 1 to assess the ADCC activity of cetuximab in conjunction with HEK293 target cells over-expressing EGFR together with CD86 resulted in an ADCC assay with an increased FL signal, increased dynamic range and increased sensitivity relative to target cells overexpressing EGFR alone (FIGS. 10B & 12B).

Figure 13A:
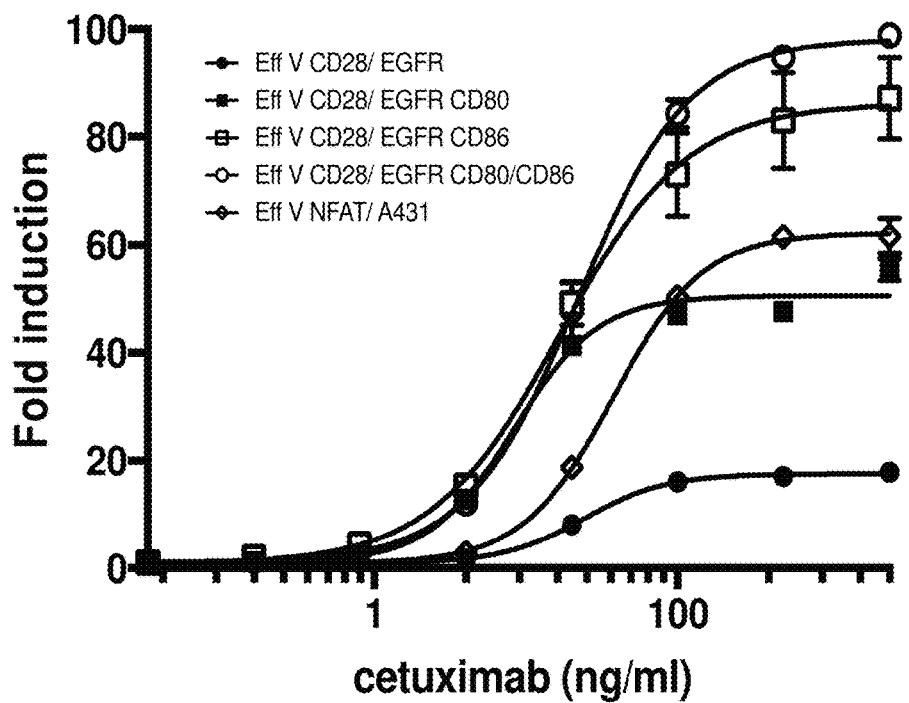
FIG. 13A illustrates a comparison of the ADCC activity of cetuximab determined using the iLite® effector cells (V-variant) over-expressing CD28 and HERK293 target cells over-expressing both EGFR and the co-stimulatory molecules CD80, or CD86, or CD80 and CD86 versus NFAT responsive effector cells (V-variant) and wild type A431 target cells.
Figure 13B:
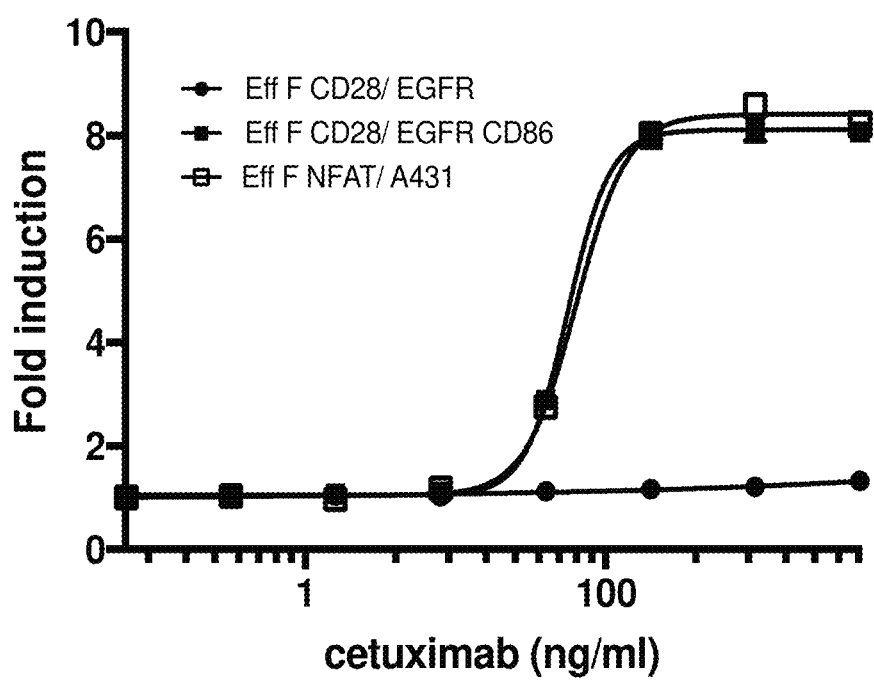
FIG. 13B illustrates a comparison of the ADCC activity of cetuximab determined using the iLite® effector cells (F-variant) over-expressing CD28 and HERK293 target cells over-expressing both EGFR and the co-stimulatory molecule CD86 versus NFAT responsive effector cells (F-variant) and wild type A431 target cells.

The use of HEK293 target cells over-expressing EGFR together with CD86 or both CD80 and CD86 to assess the ADCC activity of cetuximab in conjunction with the ADCC V-variant effector cells overexpressing the co-stimulatory receptor CD28 as described in Example 1 resulted in an ADCC assay with an enhanced dynamic range relative to an ADCC assay using NFAT responsive effector cells and wild type A431 target cells. The sensitivity of the assay was also increased using target cells overexpressing both EGFR and CD80, CD86, or both CD80 and CD86 (FIG. 13A). In contrast, the maximal FL signal observed with NFAT responsive effector cells and wild type A431 target cells was greater than that observed with the ADCC V-variant effector cells overexpressing EGFR and one or more co-stimulatory molecules (FIG. 13A, Table 3).

The use of HEK293 target cells over-expressing EGFR together with CD86 to assess the ADCC activity of cetuximab in conjunction with the ADCC effector cells expressing the F-variant of CD16A and overexpressing CD28 as described in Example 1, resulted in an ADCC assay with an increased sensitivity but unchanged dynamic range relative to an ADCC assay using NFAT responsive effector cells and wild type A431 target cells. In contrast, the maximal FL signal observed with NFAT responsive effector cells and wild type A431 target cells was greater than that observed with the ADCC F-variant effector cells overexpressing CD28 as described in Example 1 and target cells over-expressing EGFR and CD86 (FIG. 11B).

The effector cells expressing the H-131 variant of CD32A described in Example 4 expressed an enhanced FL signal, dynamic range and sensitivity when used to assess the ADCP activity of cetuximab in conjunction with recombinant HEK293 target cells over-expressing EGFR together with CD80, or CD86, or both CD80 and CD86 relative to an ADCP assay using said effector cells and target cells over-expressing EGFR alone.

The effector cells expressing the H-131 variant of CD32A described in Example 3 expressed an enhanced FL signal, dynamic range and sensitivity when used to assess the ADCP activity of cetuximab in conjunction with recombinant HEK293 target cells over-expressing EGFR together with CD80, or CD86, or both CD80 and CD86 relative to an ADCP assay using effector cells expressing FcγRIIA functionally linked to the FL reporter-gene under the control of a NFAT chimeric promoter and wild type A431 target cells.

Example 8: Establishment of an Engineered Target Cell Line Expressing High Constant Levels of mTNFα and One or More Co-Stimulatory Molecules at the Cell Surface HEK293 cells (ATCC® CRL 1573) over-expressing a constant high level of membrane bound non-cleavable TNFα (mTNFα) previously disclosed in WO 2018/065401 were transfected with the co-stimulatory molecule CD80 or CD86 or both CD80 and CD86 using the FuGENE HD transfection reagent (Promega Catalogue N° E2311). Positive clones were enriched using fluorescent activated cell sorting and phycerythrin labelled anti-CD80 (ImmunoTools, Catalogue N° 21270804) or FITC labelled anti-CD86 (ImmunoTools, Catalogue N° 21480863) monoclonal antibodies. Stable clones were isolated and characterized for ADCC activity in the presence of the ADCC effector cells previously disclosed in WO 2018/065401 and infliximab and then sub-cloned. Suitable sub-clones were isolated, characterized and propagated giving rise to a mTNFα target cell lines over-expressing CD80, or CD86 or both CD80 and CD86. Vials of iLite® effector cells disclosed in WO 2018/065401 and vials of mTNFα++ target cells over-expressing CD80, or CD86 or both CD80 and CD86 were frozen separately using standard techniques. Upon thawing, effector cells and target cells were mixed at E:T ratio of 6:1 and incubated for 6 hours in a 96-well white sided microtiter plate (Perkin Elmer 6005181) in the presence of increasing concentrations of infliximab in RPMI 1640 culture medium+10% fetal bovine serum (FBS). FL activity was then determined using the Dual Glo dual luciferase substrate and light emission was quantified in a luminometer and expressed as relative luciferase units (RLU). Results are presented as in the form of a 4-parametric logistic (4PL) plot as shown in FIGS. 6 to 9. The associated Table to the Figures and Table 4 outline the principal parameters of a 4PL plot for the iLite® effector cells and mTNFα++ target cells.

Figure 14A:
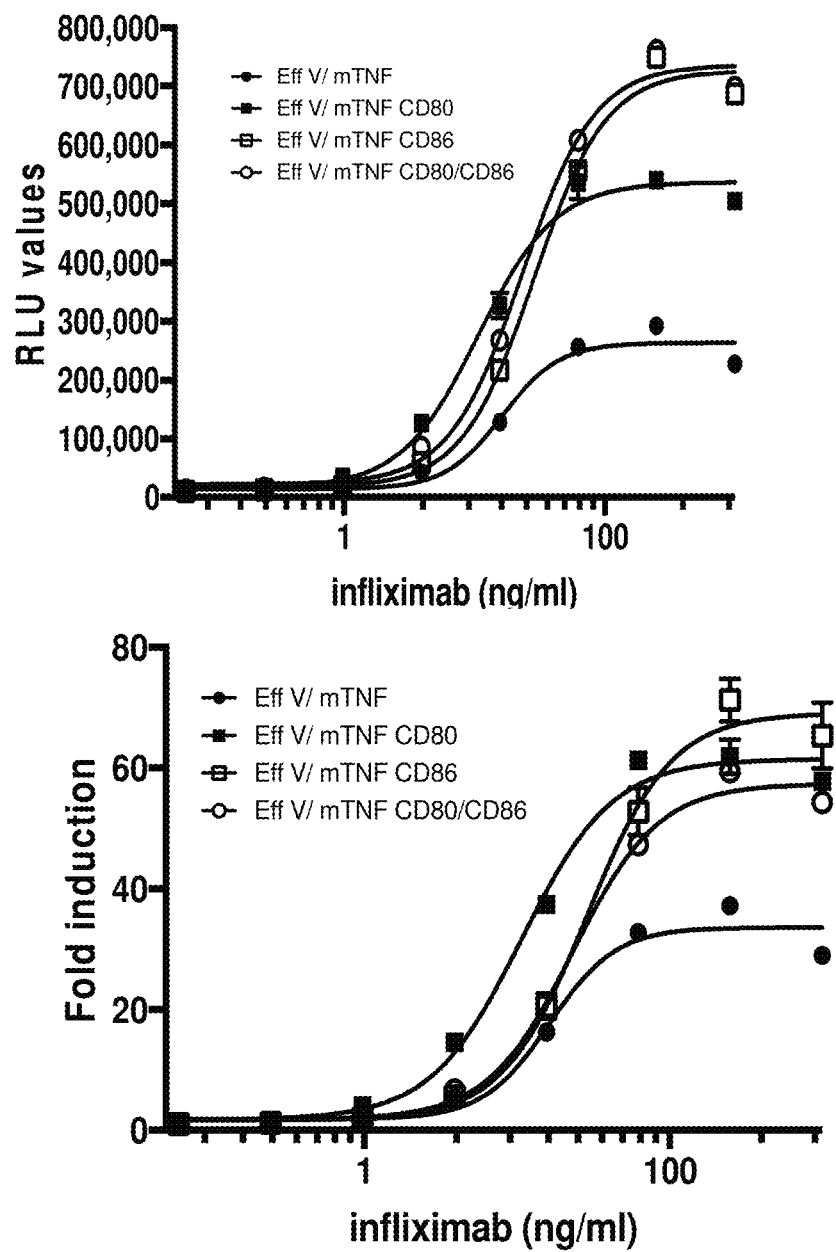
FIG. 14A illustrates the ADCC activity of infliximab determined using iLite® effector cells (V-variant) and HEK293 target cells expressing either membrane-bound TNFα alone or membrane-bound TNFα and the co-stimulatory molecules CD80, or CD86, or CD80 and CD86.

When said target cells were used to assess the ADCC activity of infliximab in conjunction with the ADCC V-variant effector cells previously disclosed in WO 2018/065401 the maximal FL signal and dynamic range of the ADCC assay were most pronounced using target cells over-expressing CD80 and CD86. An increased FL signal and dynamic range were also observed using target cells over-expressing CD80 or CD86 relative to cells over-expressing mTNFα alone (FIG. 14A, Table 4). Over expression of the co-stimulatory molecules CD80 also increased the sensitivity of the assay but not over-expression of CD86 or CD80 and CD86 together (FIG. 14A, Table 4).

Figure 14B:
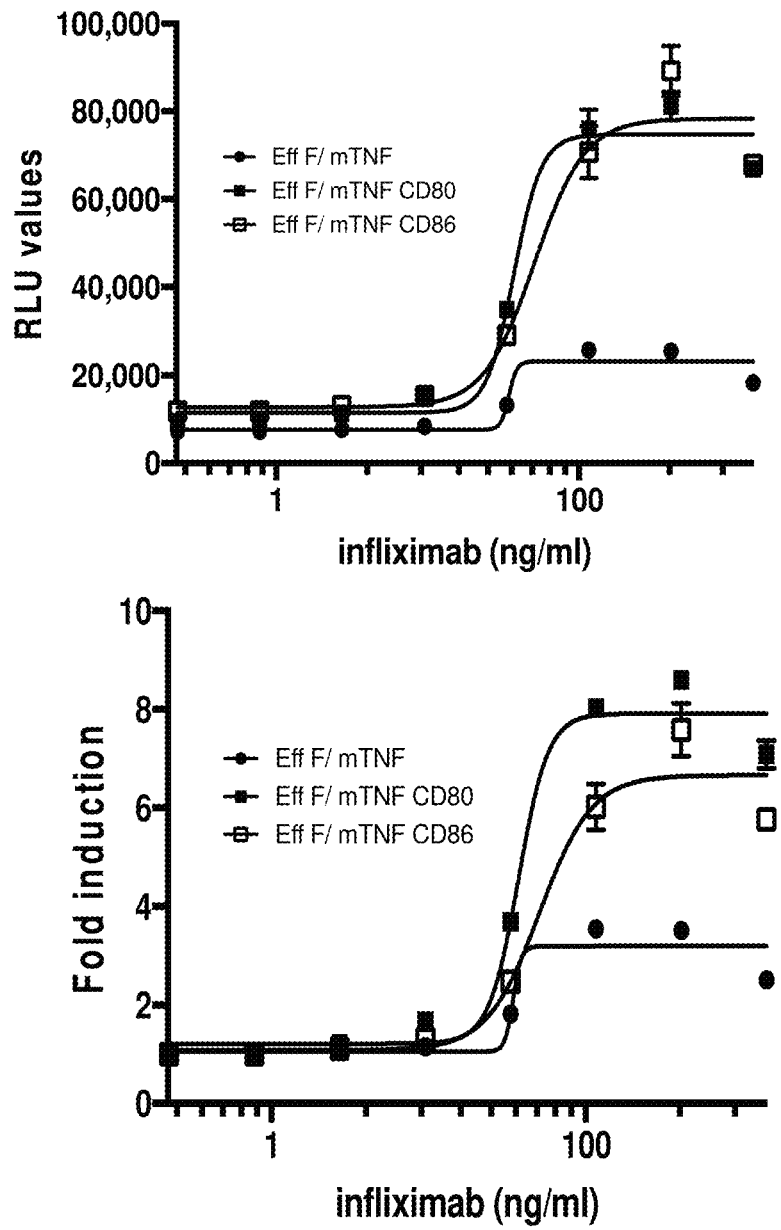
FIG. 14B illustrates the ADCC activity of infliximab determined using iLite® effector cells (F-variant) and HEK293 target cells expressing either membrane-bound TNFα alone or membrane-bound TNFα and the co-stimulatory molecules CD80 and or CD86.
Figure 15A:
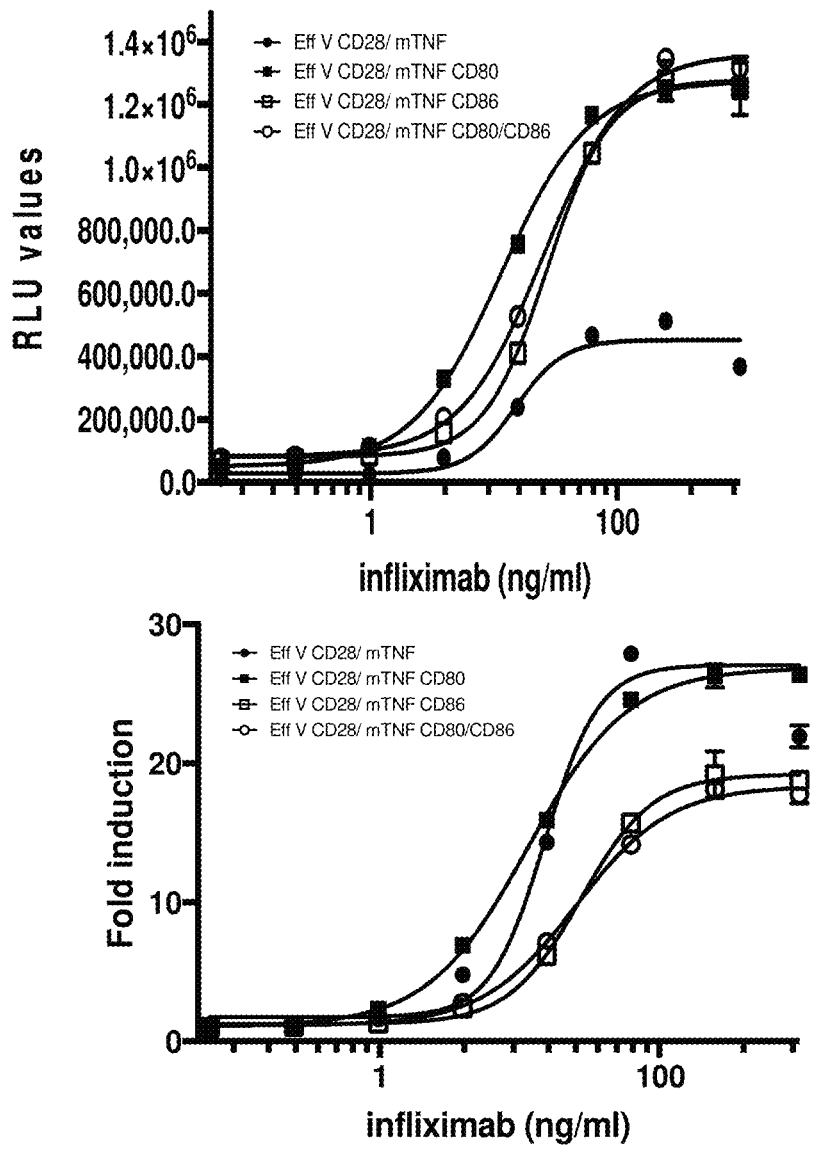
FIG. 15A illustrates the ADCC activity of infliximab determined using iLite® effector cells (V-variant) over-expressing CD28 and HEK293 target cells expressing either membrane-bound TNFα alone or membrane-bound TNFα and the co-stimulatory molecules CD80, or CD86 or CD80 and CD86.
Figure 15B:
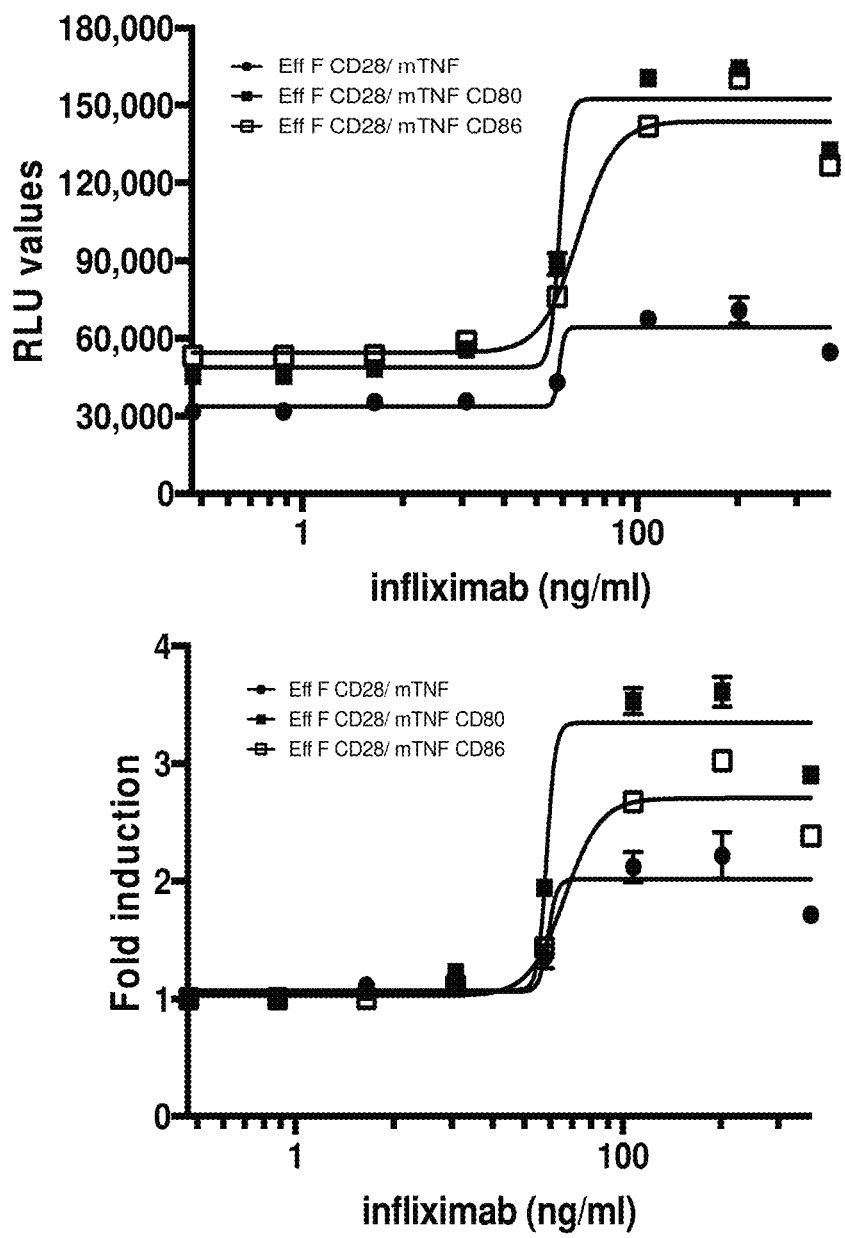
FIG. 15B illustrates the ADCC activity of infliximab determined using iLite® effector cells (F-variant) over-expressing CD28 and HEK293 target cells expressing either membrane-bound TNFα alone or membrane-bound TNFα and the co-stimulatory molecules CD80, or CD86.

The use of target cells expressing mTNFα and overexpressing one or more co-stimulatory molecules to assess the ADCC activity of infliximab in conjunction with the ADCC effector cells expressing the F-variant of CD16A previously disclosed in WO 2018/065401 resulted in an ADCC assay with an increased FL signal and dynamic range that was most pronounced using target cells over-expressing CD86 (FIG. 14B). An increased FL signal and dynamic range were also observed using target cells over-expressing CD80 relative to cells over-expressing mTNFα alone (FIG. 14B). Over expression of the co-stimulatory molecules CD80 decreased the sensitivity of the assay slightly. The decrease in sensitivity was more pronounced in target cells overexpressing both mTNFα and CD86 (FIG. 14B).

Over-expression of the co-stimulatory receptor CD28 in the recombinant Jurkat effector cells V-variant as described in Example 1 when used to assess the ADCC activity of infliximab in conjunction with HEK293 target cells expressing mTNFα together with CD80, or CD86 or both CD80 and CD86 resulted in an ADCC assay with an increased FL signal and slightly increased sensitivity in the case of target cells over-expressing the co-stimulatory molecule CD80 while the sensitivity of the assay was reduced using target cells overexpressing mTNFα together with CD86 or both CD80 and CD86 (FIG. 17A, Table 4). The dynamic range of the ADCC assay was either not affected significantly using target cells expressing both mTNFα and CD80 or decreased using target cells expressing mTNFα and CD86 or mTNFα and both CD80 and CD86 relative to the use of effector cells expressing endogenous levels of CD28 when using target cells over-expressing CD80, CD86 or CD80 together with CD86, due to an overall increase in the FL signal in both the untreated control samples and the samples treated with infliximab (FIG. 17, Table 4).

Over-expression of the co-stimulatory receptor CD28 in the recombinant Jurkat effector cells expressing the F-variant of CD16A as described in Example 1 when used to assess the ADCC activity of infliximab in conjunction with HEK293 target cells expressing mTNFα together with CD80 or CD86 resulted in an ADCC assay with an increased FL signal relative to the use of target cells expressing mTNFα alone (FIG. 17B). In contrast, the sensitivity of the assay was not affected significantly and the dynamic range of the ADCC assay was decreased relative to the use of effector cells expressing endogenous levels of CD28 when using target cells over-expressing CD86, due to an overall increase in the FL signal in both the untreated control samples and the samples treated with infliximab (FIG. 17B).

The effector cells expressing the H-131 variant of CD32A described in Example 4 expressed an enhanced FL signal, dynamic range and sensitivity when used to assess the ADCP activity of infliximab in conjunction with recombinant HEK293 target cells expressing mTNFα and overexpressing CD80, or CD86, or both CD80 and CD86 relative to an ADCP assay using said effector cells and target cells over-expressing mTNFα alone.

The effector cells expressing the H-131 variant of CD32A described in Example 4 expressed an enhanced FL signal, dynamic range and sensitivity when used to assess the ADCP activity of infliximab in conjunction with recombinant HEK293 target cells over-expressing mTNFα together with CD80, or CD86, or both CD80 and CD86 relative to an ADCP assay using effector cells expressing FcγRIIA functionally linked to the FL reporter-gene under the control of a NFAT chimeric promoter and mTNFα target cells.

In specific embodiments, the invention also relates to the following items:

Items:
1. An effector cell having a recombinant reporter gene or construct that is activated by NF-AT, AP1, NFkB, and STAT5.
2. A recombinant target cell in which the endogenous target to which an antibody is specific is invalidated.
3. A recombinant target cell in which the expression of the target to which an antibody is specific is enhanced.
4. A kit, comprising:
   an effector cell having a recombinant reporter gene assay or construct that is activated by NF-AT, AP1, NFkB, CREB, and STAT5,
   a recombinant target cell in which the endogenous target to which an antibody is specific is invalidated (dependent claims, CD20, mTNFα, erbB2 (SKBR3 & HEK293), EGFR);
   and
   recombinant target cell in which the expression of the target to which an antibody is specific is enhanced. (dependent claims, CD20, mTNFα, erbB2 (SKBR3 & HEK293), EGFR)

In specific embodiments, the invention also relates to the following Articles:

Articles:
1. An effector cell having a recombinant reporter gene or construct that is activated by NF-AT, AP1, NFkB, and STAT5.
2. A recombinant target cell in which the endogenous target to which an antibody is specific is invalidated.
3. A recombinant target cell in which the expression of the target to which an antibody is specific is enhanced.
4. A regulatory sequence which binds NF-AT, AP1, NFkB, and STAT5, comprising the nucleotide sequence disclosed in SEQ ID NO.: 1.

5. A kit, comprising:
an effector cell having a recombinant reporter gene assay or construct that is activated by NF-AT, AP1, NFkB, CREB, and STAT5;
a recombinant target cell in which the endogenous target to which an antibody is specific is invalidated (dependent claims, CD20, mTNFα, erbB2 (SKBR3 & HEK293), EGFR);
and
recombinant target cell in which the expression of the target to which an antibody is specific is enhanced. (dependent claims, CD20, mTNFα, erbB2 (SKBR3 & HEK293), EGFR).

Moreover, in further specific embodiments present invention also relates to the following notes:
Notes:
1. A vector construct comprising the polynucleotide encoding CD28.
2. A vector construct comprising the polynucleotide encoding CD137.
3. A vector construct comprising the polynucleotide encoding CD247.
4. A vector construct comprising the polynucleotide encoding CD80.
5. A vector construct comprising the polynucleotide encoding CD86.
6. A vector construct comprising the polynucleotide encoding CD137L.
7. The vector construct comprising polynucleotide SEQ ID. NO.: 1.
8. The vector according to articles 1 to 7, wherein said vector is a plasmid or viral vector.
9. A cell comprising one or more of the vectors according to any of notes 1-8.
10. The cell according to article 9, wherein the cell is a mammalian cell.
11. The cell according to notes 1 to 8, wherein said vector is episomal or integrated in the genome of said cell.
12. The cell according to any of notes 1 to 11, wherein the cell further expresses a second reporter protein which different from the first reporter protein.
13. The cell according to any of notes 1 to 12, wherein the cell is a Jurkat, Molt4, Raji, SKBR3, NK92, KHYG-1, HEK293 cells DT-40, or MSB-1
13. A kit, comprising:
i) a cell according to any of notes 9-13;
ii) a cell in which the endogenous target to which an antibody is specific is invalidated (mutated); and
iii) a cell in which the expression of the target to which an antibody is specific is enhanced.
14. The kit according to note 14, wherein the target that is invalidated in the target cells in ii) comprises one or more of CD20, mTNFα, erbB2, EGFR.
15. The kit according to note 15, wherein the target that is enhanced in the target cells in iii) comprises one or more of CD20, mTNFα, erbB2, EGFR.
16. The kit according to any of notes 14-16, wherein the kit comprises two vials.
17. The kit according to any of notes 14-16 wherein the cells in i) and iii) are present in one and the same vial at the optimal E:T ratio
18. The kit according to any of notes 14-16, wherein the ratio between the cell in i) and the target cell in iii) (E:T ratio) is in range from about 24:1 to about 2:1, or e.g. about 6:1, or about e.g. 3:1, or about e.g. 1.5:1.

In yet a further aspect, the invention relates to the following paragraphs:
1. A cell comprising a vector construct encoding one or more co-stimulatory molecules.
2. The cell according to any one the preceding paragraphs, wherein the vector construct comprises a nucleotide sequence having at least about 70% sequence identity of the nucleotide sequence set forth in SEQ ID NO.: 1.
3. The cell according to paragraph 1, wherein the vector construct further comprises a polynucleotide encoding the co-stimulatory molecule CD28.
4. The cell according to paragraph 1, wherein the vector construct further comprises a polynucleotide encoding co-stimulatory molecule CD137 (4-1BB).
5. The cell according to paragraph 1, wherein the vector construct comprises a polynucleotide encoding co-stimulatory molecule CD247 (T3 Zeta chain).
6. The cell according to paragraph 1, wherein the vector construct comprises a polynucleotide encoding co-stimulatory molecule CD278 (ICOS).
7. The cell according to any of the preceding paragraphs, wherein co-stimulatory molecules are receptors selected from one or more of CD28, CD137L (4-1BB), and ICOS.
8. The cell according to any of the preceding paragraphs, wherein the one or more co-stimulatory molecules are expressed constitutively or over-expressed on the cells.
9. The cell according to any of the preceding paragraphs, wherein the cells further express CD16A or CD32.
10. The cell according to any of the preceding paragraphs, wherein CTLA-4 (CD152) is specifically invalidated.
11. The cell according to any of the preceding paragraphs, wherein the cell is a primary cell or a cell line.
12. The cell according to any of the preceding paragraphs, wherein the cell is an animal cell line such as e.g. Jurkat, Molt4, Raji, SKBR3, NK92, KHYG-1, HEK293 cells DT-40, or MSB-1.
13. The cell according to any of the preceding paragraphs, wherein said vector is episomal or integrated in the genome of said cell.
14. The cell according to any of the preceding paragraphs, wherein the cell further expresses a first reporter protein.
15. The cell according to any of the preceding paragraphs, wherein the first reporter protein is an enzyme such as e.g. a luciferase or a fluorescent protein.
16. The cell according to any of the preceding paragraphs, wherein the cell further expresses a second reporter protein which different from the first reporter protein.
17. The cell according to any of the preceding paragraphs, wherein the cell further expresses an antigen recognized by an antibody or Fc fusion protein.
18. The cell according to any of the preceding paragraphs, wherein the cell further overexpresses an antigen recognized by an antibody or Fc fusion protein.
19. A kit, comprising:
i) an effector cell (E), capable of binding to the Fc region of an antibody and expressing one or more co-stimulatory molecules or overexpressing one or more co-stimulatory molecules according to any of paragraphs 1-18;
ii) a target cell (T−) in which the endogenous target/antigen to which said antibody is specific is invalidated (mutated) such that the target/antigen is not expressed by the cell or expressed in a non-functional form; and
iii) a target cell (T+) in which the expression of the target to which said antibody is specific is enhanced or overexpressed together with one or more co-stimulatory molecules including CD80, CD86, CD137L, and (CD278L) ICOSL.

20. A kit according to paragraph 19, wherein the cell in ii) and the cell iii) are exactly the same cell identical in all respects except the cell in ii) does not express a specific antigen recognized by the antibody or drug being assayed.

21. The kit according to any one of paragraphs 19-20, wherein the target/antigen is one or more of CD20, mTNFα, erbB2, EGFR.

22. The kit according to any of paragraphs 19-21, wherein the kit comprises two vials and wherein the cells in i) and iii) are present in one and the same vial at the optimal E:T ratio.

23. The kit according to any of paragraphs 19-22, wherein the ratio between the effector cell in i) and the target cell in iii) (E:T ratio) is in range from about 24:1 to about 2:1, or about 6:1, or about 3:1, or about 1.5:1.

24. A method for quantifying the Antibody-Dependent Cell-mediated Cytotoxicity (ADCC) activity of therapeutic antibodies, the method comprising the steps of;
a) contacting a sample obtained containing an antibody, with effector cell i) and target cells iii) according to paragraph 19 iii),
b) subtracting the signal obtained in the presence of effector cells i) and cells ii) according to paragraph 19 ii), in which the drug target has been invalidated, from the signal obtained in the presence of effector cells i) according to any one of paragraphs 1-18 and target cells iii) according to paragraph 19iii),
c) determining the ADCC activity on the basis of the signal relationship as measured in a) and b).

25. A method for quantifying the Antibody-Dependent Cell-mediated Phagocytosis (ADCP) activity of therapeutic antibodies, the method comprising the steps of;
a) contacting a sample obtained containing an antibody, effector cells i) and with target cells iii) according to paragraph 19iii),
b) subtracting the signal obtained in the presence of effector cells i) and cells ii) according to paragraph 19 ii), in which the drug target has been invalidated, from the signal obtained in the presence of effector cells i) according to any one of paragraphs 1-18 and target cells iii) according to paragraph 19iii),
c) determining the ADCP activity on the basis of the signal relationship as measured in a) and b).

REFERENCES

1. Parekh, B. S., et al. Development and validation of an antibody-dependent cell-mediated cytotoxicity reporter gene assay. mABs 4:3, 310-318, 2012
2. Cheng, Z. J., et al. Development of a robust reporter-based ADCC assay with frozen, thaw-and-use cells to measure Fc effector function of therapeutic antibodies. J. Immunol., Methods, 414:69-81, 2014.
3. Lallemand, C. et al., A Novel System for the Quantification of the ADCC Activity of Therapeutic Antibodies. J. immunol. Res. 1-17, 2017
4. Lallemand et al. Reporter gene assay for the quantification of the activity and neutralizing antibody response to TNFα antagonists. J. Immunol. Methods, 373:229-239, 2011.
5. Tatsumi, T., et al, expression of co-stimulatory molecules B7-1 (CD80) and B7-2 (CD86) on human hepatocellular carcinoma; Hepatology, 25:1108

The invention claimed is:

1. A cell for the purpose of enhanced dynamic range and increased sensitivity in detection of Antibody-Dependent Cell-mediated Cytotoxicity (ADCC) or Antibody-Dependent Cell-mediated Phagocytosis (ADCP) activity, the cell comprising a viral vector or plasmid encoding (i) a one or more co-stimulatory molecule selected from the group consisting of: CD28, CD137 (4-1BB), CD247 (T3 Zeta chain), CD278 (ICOS), wherein the one or more co-stimulatory molecule is constitutively expressed or over-expressed by the cell; and (ii) a nucleotide sequence SEQ ID NO.:1, wherein SEQ ID NO.: 1 is GGAAGCGAAA ATGAAATTGA CTGGGACTTT CCGGAGGAAA AACTGTTTCA TACAGAAGGC GTGGATGTCC ATATTAGGAT GAGTCAGTGA CGTCAGAGCC TGATTTCCCC GAAATGATGA GCTAG.

2. The cell according to claim 1, wherein the one or more co-stimulatory molecules are expressed constitutively or over-expressed on the cells.

3. The cell according to claim 1, wherein the molecular construct further encodes CD16A or CD32.

4. The cell according to claim 1, wherein a CTLA-4 (CD152) is specifically invalidated.

5. The cell according to claim 1, wherein the cell is a primary cell or a cell line.

6. The cell according to claim 1, wherein the cell is an animal cell.

7. The cell according to claim 1, wherein the molecular construct is an episome or is integrated into the genome of the cell.

8. The cell according to claim 1, wherein the cell further encodes a first reporter protein.

9. The cell according to claim 8, wherein the first reporter protein is an enzyme and wherein the enzyme is a luciferase or a fluorescent protein.

10. The cell according to claim 8, wherein the cell further encodes a second-reporter protein which is different from the first reporter protein.

11. The cell according to claim 1, wherein the cell further encodes an antigen recognized by an antibody or a Fc fusion protein.

12. A kit, comprising:
   i) an effector cell (E), according to claim 1, and capable of binding to a Fc region of an antibody;
   ii) a target cell (T−) in which an endogenous target/antigen to which the antibody is specific is invalidated (mutated) such that the target/antigen is not expressed by the T− cell or is expressed in a non-functional form; and
   iii) a target cell (T+) in which the expression of a target to which the antibody is specific is enhanced or is overexpressed together with one or more co-stimulatory molecules including CD80, CD86, CD137L, or (CD278L) ICOSL.

13. A kit according to claim 12, wherein the cell in ii) and the cell iii) are exactly the same cell identical in all respects except the cell in ii) does not express a specific antigen recognized by the antibody or drug being assayed.

14. The kit according to claim 12, wherein the target/antigen is one or more of CD20, mTNFα, erbB2, EGFR.

15. The kit according to claim 12, wherein the kit comprises the cells in i) and iii) in the same vial at the optimal E:T ratio, wherein the ratio between the effector cell in i) and the target cell in iii) (E:T ratio) is in range from about 24:1 to about 2:1, or about 6:1, or about 3:1, or about 1.5:1.

16. A method for quantifying the Antibody-Dependent Cell-mediated Cytotoxicity (ADCC) activity of therapeutic antibodies, the method comprising the steps of;
   a) contacting a sample obtained containing an antibody, with effector cell (E) i) according to claim 1 i) and target cells iii) according to claim 1 iii),
   b) subtracting the signal obtained in the presence of effector cells (E) i) and cells ii) according to claim 1 ii), in which the drug target has been invalidated, from the signal obtained in the presence of effector cells (E) i) according to claim 1 and target cells iii) according to claim 1 iii),
   c) determining the ADCC activity on the basis of the signal relationship as measured in a) and b).

17. A method for quantifying the Antibody-Dependent Cell-mediated Phagocytosis (ADCP) activity of therapeutic antibodies, the method comprising the steps of;
   a) contacting a sample obtained containing an antibody, effector cells (E) i) according to claim 1 i) and with target cells iii) according to claim 1 iii),
   b) subtracting the signal obtained in the presence of effector cells (E) i) according to claim 1 i) and cells ii) according to claim 1 ii), in which the drug target has been invalidated, from the signal obtained in the presence of effector cells i) according to claim 1 and target cells iii) according to claim 1 iii),
   c) determining the ADCP activity on the basis of the signal relationship as measured in a) and b).

* * * * *

SEQUENCE LISTING

```
<160> NUMBER OF SEQ ID NOS: 1

<210> SEQ ID NO 1
<211> LENGTH: 125
<212> TYPE: DNA
<213> ORGANISM: Artificial sequence
<220> FEATURE:
<223> OTHER INFORMATION: Synthetic

<400> SEQUENCE: 1
ggaagcgaaa atgaaattga ctgggacttt ccggaggaaa aactgtttca tacagaaggc      60
gtggatgtcc atattaggat gagtcagtga cgtcagagcc tgatttcccc gaaatgatga    120
gctag                                                                125
```